(12) United States Patent
Shirai et al.

(10) Patent No.: US 12,031,176 B2
(45) Date of Patent: Jul. 9, 2024

(54) CELL ANALYSIS DEVICE, APPARATUS, AND CELL ANALYSIS METHOD USING SAME

(71) Applicant: HITACHI HIGH-TECH CORPORATION, Tokyo (JP)

(72) Inventors: Masataka Shirai, Tokyo (JP); Tomoyuki Sakai, Tokyo (JP); Kenko Uchida, Tokyo (JP)

(73) Assignee: HITACHI HIGH-TECH CORPORATION, Tokyo (JP)

( * ) Notice: Subject to any disclaimer, the term of this patent is extended or adjusted under 35 U.S.C. 154(b) by 1016 days.

(21) Appl. No.: 16/940,517

(22) Filed: Jul. 28, 2020

(65) Prior Publication Data

US 2020/0354781 A1    Nov. 12, 2020

Related U.S. Application Data

(62) Division of application No. 15/775,408, filed as application No. PCT/JP2015/083719 on Dec. 1, 2015, now Pat. No. 10,752,941.

(51) Int. Cl.
*C12Q 1/68* (2018.01)
*C12N 15/10* (2006.01)
(Continued)

(52) U.S. Cl.
CPC ....... *C12Q 1/6837* (2013.01); *C12N 15/1003* (2013.01); *C12N 15/1093* (2013.01);
(Continued)

(58) Field of Classification Search
CPC ....... C12Q 1/6837; C12Q 1/68; C12Q 1/6806
See application file for complete search history.

(56) References Cited

U.S. PATENT DOCUMENTS 6,716,629 B2    4/2004    Hess et al.
10,030,240 B2   7/2018    Shirai et al.
(Continued)

FOREIGN PATENT DOCUMENTS

CN    102911864 A    2/2013
CN    105026562 A    11/2015
(Continued)

OTHER PUBLICATIONS

International Search Report of PCT/JP2015/083719 dated Feb. 16, 2016.

*Primary Examiner* — Stephanie K Mummert
(74) *Attorney, Agent, or Firm* — MATTINGLY & MALUR, PC

(57) ABSTRACT

The purpose of the present invention is to provide a single cell analysis device in which the improvement of the nucleic acid capturing efficiency and the improvement of the cell capturing efficiency are both achieved and a highly accurate single cell analysis data is thereby obtained. The present invention relates to an improvement of a cell analysis device including a two-dimensional array chip having a plurality of cell capture parts capable of capturing a single cell in each of the capture parts, and nucleic acid capture parts corresponding to the respective cell capture parts, the nucleic acid capture parts being capable of capturing a nucleic acid extracted from the cell captured by the cell capture part.

7 Claims, 11 Drawing Sheets

(51) Int. Cl.
    *C12Q 1/6806* (2018.01)
    *C12Q 1/6809* (2018.01)
    *C12Q 1/6837* (2018.01)
    *C40B 40/08* (2006.01)
    *C40B 50/06* (2006.01)
    *G01N 33/543* (2006.01)

(52) U.S. Cl.
    CPC ........... *C12N 15/1096* (2013.01); *C12Q 1/68* (2013.01); *C12Q 1/6806* (2013.01); *C12Q 1/6809* (2013.01); *C40B 40/08* (2013.01); *C40B 50/06* (2013.01); *G01N 33/54306* (2013.01)

(56) References Cited

U.S. PATENT DOCUMENTS

| | | |
|---|---|---|
| 2012/0245053 A1 | 9/2012 | Shirai et al. |
| 2013/0071946 A1* | 3/2013 | Burghardt .............. G01N 1/405 422/69 |
| 2015/0167063 A1* | 6/2015 | Shirai ................ C12N 15/1096 506/9 |
| 2016/0010078 A1 | 1/2016 | Shirai et al. |

FOREIGN PATENT DOCUMENTS

| | | |
|---|---|---|
| JP | 2015-097499 A | 5/2015 |
| WO | 2011/068088 A1 | 6/2011 |
| WO | 2014/020657 A1 | 2/2014 |

* cited by examiner (C)

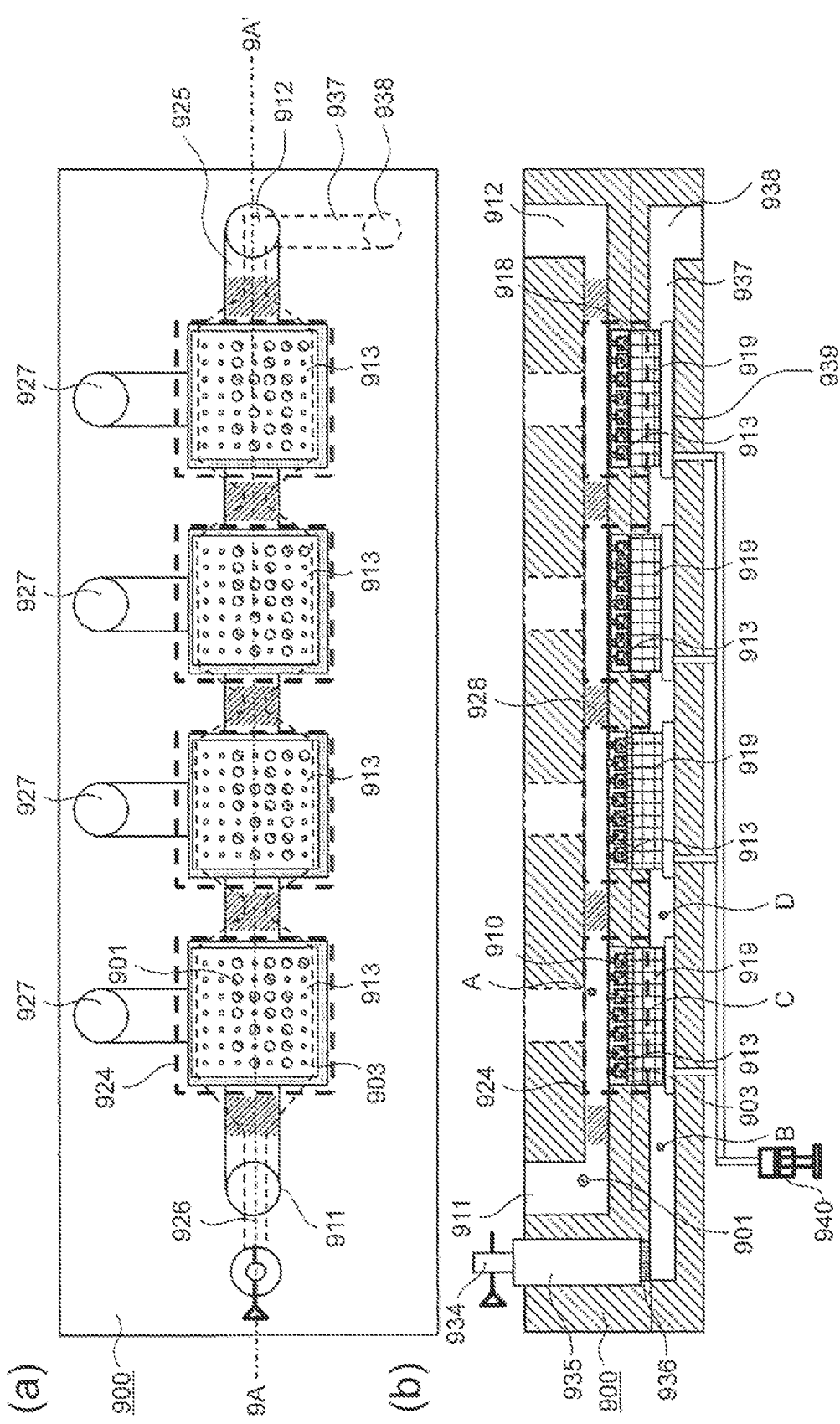

CELL ANALYSIS DEVICE, APPARATUS, AND CELL ANALYSIS METHOD USING SAME

TECHNICAL FIELD

The present invention relates to the technical fields of gene expression analysis, cell function analysis, biological tissue analysis method, disease diagnosis, drug discovery, and the like, and more specifically, relates to a cell analysis device, an apparatus and a cell analysis method using the same which makes the genetic analysis for a single cell possible.

BACKGROUND ART

Single cell analysis is a technique for detecting and/or quantifying with high accuracy biomolecules in cells for every single cell. To perform the single cell analysis, it is necessary to isolate cells for separate treatments, efficiently extract nucleic acids to be measured from the cells, synthesize a complementary chain (for example, cDNA), and if needed, perform sequence analysis of a product obtained by amplification.

Patent Document 1 discloses a device configured to capture respective cells in each pores of a porous array sheet, subsequently, capture a nucleic acid derived from the cell with a DNA probe that is immobilized in the pore and that has a different tag sequence for each pore to synthesize cDNA, and thus can obtain a product for sequence analysis capable of distinguishing from which cell the captured nucleic acid has been derived. The basic configuration (corresponding to FIG. 8 of Patent Document 1) of such device is shown in FIG. 1.

In the device of FIG. 1, a cell solution containing cells 101 is introduced from an inlet 106. The cell solution is sucked from an upper outlet 107 in order to fill an upper region 104 of a porous membrane 102 having a planar substrate shape with the cell solution. If a negative pressure is applied by sucking the solution from a lower outlet 108, the cell solution is sucked through the porous membrane 102, and the cells 101 are guided to a cell capture part 103. The cells 101 are captured by a lattice-shaped cell capture part 103 constructed on the porous membrane 102, and then, by disrupting the cells, the nucleic acids (for example, mRNA) within the cells are captured by a DNA probe (for example, a poly-T probe) immobilized within the porous membrane directly beneath the cells.

By using a device as shown in FIG. 1, the nucleic acids extracted from the captured cells can be captured with hardly any contact with regions other than the inner wall of the porous membrane which is the reaction region, and the nucleic acid (for example, cDNA) corresponding to the captured nucleic acid can be synthesized. Therefore, the probability that nucleic acids are adsorbed on the inner wall of the device unrelated to the reaction can be reduced, and a product for sequence analysis can be prepared highly efficiently.

PRIOR ART DOCUMENT

Patent Document

Patent Document 1: WO2014/020657 A

SUMMARY OF THE INVENTION

Problem to be Solved by the Invention

To efficiently capture nucleic acids in the device as shown in FIG. 1, it is necessary that the average pore diameter of the pores constituting the porous membrane 102 is several μm or less, and especially, 1 μm or less is preferable. Further, it is desirable that the thickness of the porous membrane 102 is 10 μm or more, especially, several tens of μm or more. However, if such porous membrane is used, the pressure loss when the cell solution passes therethrough becomes large. If the pressure loss becomes large, the suction rate decreases upon suctioning the solution from the lower outlet 108. This results in that the suction rate of suctioning the cells 101 into the cell capture part 103 decreases. Therefore, the phenomenon that a relatively large number of cells settle with gravity, and remain in the other regions on the device before reaching the cell capture part 103 has been observed. The cell indicated by 109 in FIG. 1 is one example of a cell which did not reach such cell capture part 103.

The cells remaining in the regions other than the cell capture part 103 not only reduce the ratio of cells that can be analyzed but also cause an additional problem. That is, when extracting nucleic acids from cells, a step for disrupting the cells is necessary. However, upon that, cells present in regions other than the cell capture part 103 are also disrupted. Owing to this, there arises a problem that the nucleic acids extracted from the cells flow in a plurality of cell capture parts 103 and it becomes difficult to perform an accurate single cell analysis.

The above problems are caused by an increase of the pressure loss due to the increase of the membrane thickness and a decrease of the pore diameter of the porous membrane 102, which are intended for improving the nucleic acid capturing efficiency. Therefore, the problem essentially lies in the fact that the improvement of the nucleic acid capturing efficiency and the improvement of the cell capturing efficiency are in a trade-off relationship.

Furthermore, a nucleic acid amplification step is necessary to perform sequence analysis after the capturing of the nucleic acid. In this step, it is necessary that the nucleic acid amplification product is released from the nucleic acid capture part (as described in Patent Document 1), extracted to the outside of the device as the solution sample, and sequence analysis is performed. There may arise a problem that the amplification product within this solution is adsorbed on the inner wall of the device. The yield of the nucleic acid amplification product necessary for sequence analysis is reduced by adsorption. In addition, since the adsorption rates differ in accordance with the difference in the base length of the nucleic acids, sequence analysis may possibly be performed with a composition which is different from the composition of the original nucleic acid in the cell.

Means for Solving the Problem

The present inventors examined the above-mentioned problems, and as a result, found the followings. It is effective to make this device structure such that a repulsive force which causes the cells not to approach the region on the substrate other than the cell capture part is applied to the cells when a cell solution is sucked from the back surface of the substrate (for example, the porous membrane) on which the nucleic acid capture part is provided. Namely, as one example, the device configured so as to apply gravity to the cells in a direction opposite to the suction direction to the cells as shown in FIG. 2 is effective. In addition to the gravity as exemplified in FIG. 2, an electrostatic force caused by the surface treatment or an electrophoretic force can be effectively adopted as such repulsive force.

Further, the present inventors found that the method of using a second three-dimensional porous membrane (three-dimensional porous member) as shown in FIG. 3 to strengthen the suction force to thereby prevent adsorption in the regions other than the cell capture part due to other forces. However, since the inner wall of the second three-dimensional porous membrane needs to be hydrophilic, it is highly likely that a DNA stand having a negative charge will be adsorbed on the inner wall. Therefore, the yield of the obtained amplification product may decrease, and a change in the yield due to the length of the DNA amplification product may occur, thus, the analysis of the nucleic acid composition in a single cell may be difficult. To further improve this point, it has been found that it is effective to provide a means for separating the hydrophilic three-dimensional porous membrane and the solution of the nucleic acid capture part which becomes the amplification reaction part in the amplification reaction process. As the means for performing such separation, it has been found that it is effective to provide a means for injecting air or a nonpolar solvent such as oil at an appropriate time between a first porous membrane (or substrate, i.e., the two-dimensional array chip) which is the nucleic acid capture part and a second hydrophilic three-dimensional porous membrane for suction assistance, or, provide an actuator inside the device that causes the distance between the placed first and the second porous membranes in a vertical direction with respect to the membranes becomes large. Furthermore, it has been found that it is effective to use a separation membrane such as an ultrafiltration membrane or gel membrane between the first and the second porous membranes such that the amplification product does not reach the second porous membrane.

Therefore, the summary of the present invention is as follows:

(1) A cell analysis device comprising:
a solution introduction channel for introducing a solution containing cells;
a substrate having a plurality of sets of a cell capture part and a nucleic acid capture part, the cell capture part being in contact with the solution introduction channel and having a concavity capable of capturing a single cell, and the nucleic acid capture part being provided in a corresponding manner to the concavity of the cell capture part and capturing a nucleic acid extracted from the cell having been captured by the cell capture part;
a discharge channel that is provided adjacent to the nucleic acid capture part of the substrate, and discharges a solution of the nucleic acid capture part; and
a pressure control means provided in the discharge channel,
in which the substrate has a repulsive force in a direction which separates the cells from the substrate, and
the pressure control means controls such that, when the cell is captured by the cell capture part, a force in the direction from the cell capture part to the nucleic acid capture part serves as a first pressure that is larger than the repulsive force.
(2) The cell analysis device according to (1), in which the pressure control means controls such that, when performing the nucleic acid reaction in the nucleic acid capture part, the force in the direction from the cell capture part to the nucleic acid capture part is larger than gravity and smaller than the first pressure.
(3) The cell analysis device according to (1), in which a region which is on the substrate other than the concavity and which is in contact with the solution containing the cells is a region that exerts a repulsive force on the cells.
(4) The cell analysis device according to (1), in which the repulsive force is a repulsive force caused by the substrate being placed in such a manner that the cell capture part captures the cell in the direction counter to gravity.
(5) The cell analysis device according to (1), in which the repulsive force is a repulsive force caused by the surface of the substrate having been subjected to a treatment which prevents the adsorption of cells.
(5-1) The cell analysis device according to (5), in which the treatment which prevents the adsorption of cells is a surface treatment by a coating agent, for example, MPC polymer.
(6) The cell analysis device according to (1), further comprising an electrode pair provided so as to sandwich the substrate, in which the nucleic acid capture part comprises metal microparticles, and the repulsive force is a repulsive force caused by a voltage applied to the electrode pair and dielectric coupling by the metal microparticles.
(6-1) The cell analysis device according to (6), in which the metal microparticles are gold microparticles, and/or the substrate is a platinum substrate.
(7) A cell analysis device comprising:
a solution introduction channel for introducing a solution containing cells,
a two-dimensional array chip having a plurality of cell capture parts and nucleic acid capture parts, the cell capture parts being provided adjacent to the solution introduction channel and each being capable of capturing a single cell, and each of the nucleic acid capture parts being provided corresponding to each cell capture part of the plurality of cell capture parts and capturing a nucleic acid extracted from the cell having been captured by the cell capture part,
a discharge channel having a three-dimensional porous body which absorbs a solution retained in the nucleic acid capture part and for discharging the solution, and
a separation control part for controlling separation between the nucleic acid capture part and the discharge channel,
in which the separation control part performs separation control such that, after the nucleic acid is captured by the nucleic acid capture part, a product amplified from the captured nucleic acid is not introduced into the discharge channel.
(8) The cell analysis device according to (7), in which the separation control part is a suction pressure application means provided in the discharge channel.
(9) The cell analysis device according to (7), in which an ultrafiltration membrane or a gel membrane for preventing the passage of molecules having the molecular size of the amplified product is disposed between the two-dimensional array chip and the three-dimensional porous body.
(10) The cell analysis device according to (7), in which the separation control part is a means for introducing a separation solvent or air between the nucleic acid capture part and the discharge channel.
(10-1) The cell analysis device according to (10), in which the separation solvent is mineral oil.
(11) The cell analysis device according to (1) or (7), in which the nucleic acid capture part comprises a nucleic acid probe for capturing a nucleic acid, and the nucleic acid probe comprises a nucleic acid capture sequence which hybridizes with the nucleic acid extracted from the cell and a cell recognition sequence which is different corresponding to the respective cell capture part.
(12) A cell analysis method using the cell analysis device according to (1), including the steps of
filling the substrate with a solution containing cells; and
applying a negative pressure to the cell capture part, sucking the solution containing the cells in direction to the substrate, and capturing a single cell on the cell capture part.
(13) The cell analysis method according to (12), further including steps of disrupting the single cell captured on the cell capture part in a state in which a negative pressure is applied to the cell capture part, and capturing the nucleic acid extracted from the cell by the nucleic acid capture part.
(14) The analysis method according to (13), further including a step of supplying to the nucleic acid capture part, a second nucleic acid probe having a sequence which hybridizes with the nucleic acid captured by the nucleic acid capture part, and an enzyme and a substrate for complementary strand synthesis which uses the captured nucleic acid as a template to perform complementary strand synthesis.
(15) A cell analysis method using the cell analysis device according to (7), including the steps of
filling a solution containing cells on the two-dimensional array chip; and
applying a negative pressure to the cell capture part, sucking the solution containing the cells from the discharge channel provided with the three-dimensional porous body, and introducing a reagent for nucleic acid amplification to the nucleic acid capture part by suction in the same manner as the solution containing the cells, and then, separating the nucleic acid capture part or the two-dimensional array chip from the three-dimensional porous body until before the start of the amplification reaction or after the start and until before the end of the amplification reaction.
(15-1) The cell analysis method according to (15), further including a step for disrupting the single cell captured on the cell capture part in a state in which a negative pressure is applied to the cell capture part, and capturing the nucleic acid extracted from the cell by the nucleic acid capture part.
(15-2) The analysis method according to (15-1), further including a step for supplying to the nucleic acid capture part, the second nucleic acid probe having a sequence which hybridizes with the nucleic acid captured by the nucleic acid capture part, and an enzyme and a substrate for complementary strand synthesis which uses the captured nucleic acid as a template to perform complementary strand synthesis.
(16) A cell analyzer including the cell analysis device according to any one of (1) to (11), and a cell observation means (for example, a fluorescence microscope).

Effect of the Invention

The cell analysis device, apparatus and cell analysis method of the present invention has succeeded in improving the cell capturing efficiency in the cell capture part, compared with the conventional techniques, while maintaining the nucleic acid capturing efficiency in the nucleic acid capture part when performing nucleic acid capture from cells. As a result, it becomes possible to prepare a sample for single cell analysis in which the degree of separating the respective cells is accurately made higher than that by using the conventional devices and the like. Further, according to the cell analysis device, the apparatus and the cell analysis method of the present invention, it becomes possible to collect the amplification product with high efficiency when performing the amplification reaction inside the device.

Therefore, according to the cell analysis device, the apparatus and the cell analysis method of the present invention, it is possible to quantitatively analyze, with high efficiency and high accuracy, not only the expression level of genes as the average of tissues but also the contents of the respective cells constituting tissues. By performing single cell analysis which measures, at the single cell level, genes (for example, mRNA) which are active in living tissue, it is possible to know various phenomena occurring in vivo in detail including the interaction between cells. This is expected to have a large effect on the life sciences field, specifically, medicine, drug discovery, diagnosis, basic research of vital phenomena, and the like.

BRIEF DESCRIPTION OF DRAWINGS

FIG. 8-1 is a figure showing an outline of the configuration of the device according to Example 2.
FIG. 8-2 is the continuation of FIG. 8-1.
FIG. 9 is a figure showing an outline of the configuration of the device manufactured in Example 2-2.

MODES FOR CARRYING OUT THE INVENTION

In one aspect, when sucking the cells in the cell capture part of the two-dimensional array chip, the cell analysis device of the present invention prevents the adsorption of the cells on the two-dimensional array chip by sucking the cells in competition with a repulsive force (for example, gravity) in the direction which separates the cells from the substrate of the two-dimensional array chip. Specifically, the cell analysis device of the present invention includes: a solution introduction channel for introducing a solution containing cells; a substrate having a plurality of sets of a cell capture part and a nucleic acid capture part, the cell capture part being in contact with the solution introduction channel and having a concavity capable of capturing a single cell, and the nucleic acid capture part being provided in a corresponding manner to the concavity of the cell capture part and capturing a nucleic acid extracted from the cell having been captured by the cell capture part; a discharge channel that is provided adjacent to the nucleic acid capture part of the substrate, and discharges a solution of the nucleic acid capture part; and a pressure control means provided in the discharge channel. The substrate has a repulsive force in a direction which separates the cells from the substrate. The pressure control means controls such that, when the cell is captured by the cell capture part, a force in the direction from the cell capture part to the nucleic acid capture part serves as a first pressure that is larger than the repulsive force.

Figure 2:
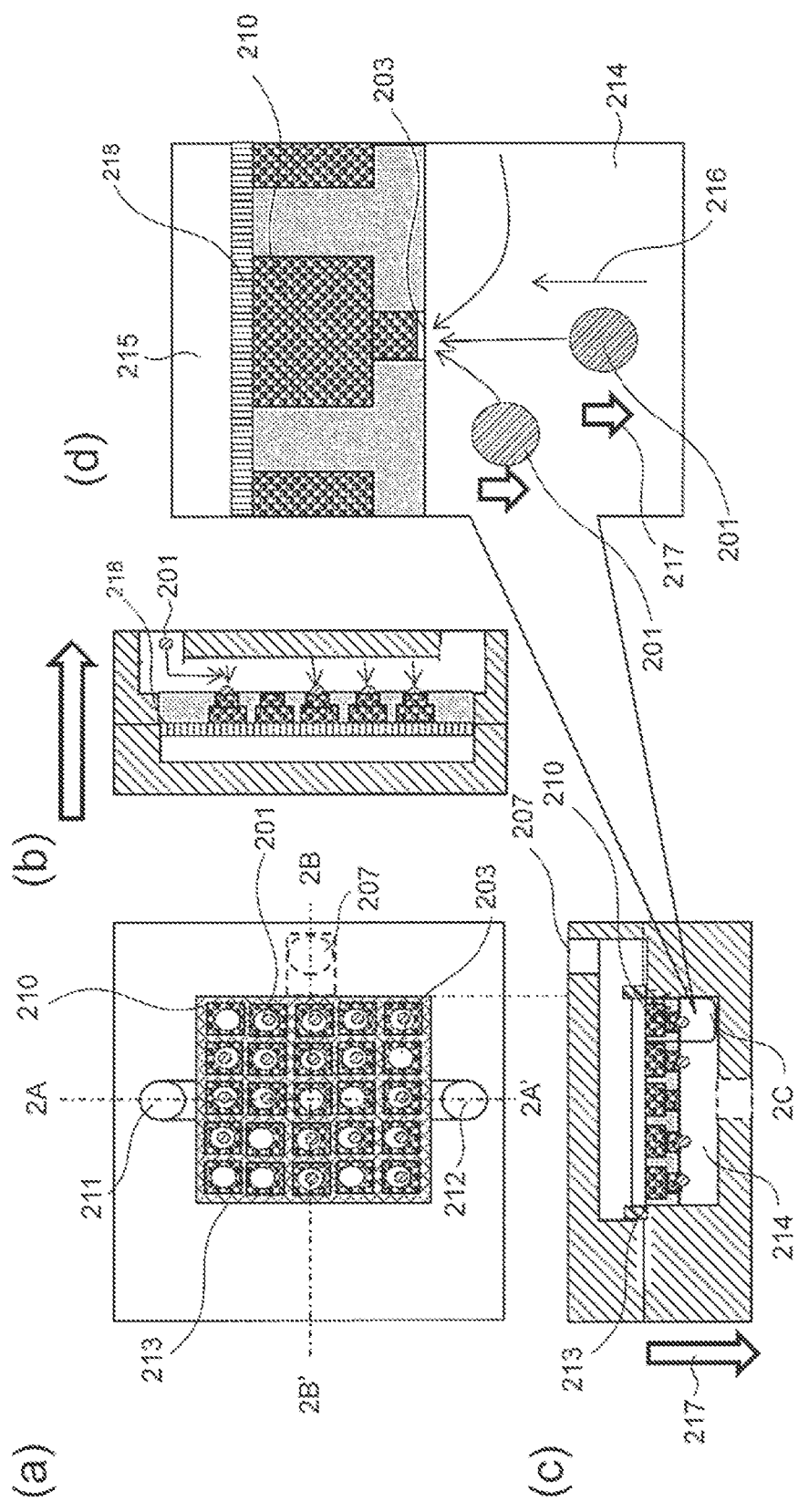
FIG. 2 is a figure showing an embodiment having the configuration of a cell analysis device according to an aspect of the present invention.

FIG. 2 is a figure showing an embodiment of the configuration of the cell analysis device according to the above aspect of the present invention, (a) shows a bottom view (plan view seen from the bottom), (b) shows a cross-sectional view in the 2A-2A' cross section, and (c) shows a cross-sectional view in the 2B-2B' cross section. Further, (d) is an enlarged view of the region 2C in the cross-sectional view (c).

The cell analysis device according to the present invention includes a substrate (hereinafter, referred to as the two-dimensional array chip (213)) having sets of followings: a plurality of cell capture parts 203 each of which can capture a single cell; and nucleic acid capture parts 210 disposed corresponding to the respective cell capture parts and capturing nucleic acids extracted from the cells captured by the cell capture parts. A lower region 214 which holds a cell solution introduced from a cell introduction port 211 prior to sucking is provided adjacent to the two-dimensional array chip. An upper region 215 of the opposite side is connected to an upper outlet 207 on the upper side. A pump or a syringe is connected to the upper outlet 207. By applying a negative pressure to the upper outlet 207, a negative pressure can be applied to the nucleic acid capture parts 210 and the cell capture parts 203 on the two-dimensional array chip, and the cell solution within the region 214 is sucked into the cell capture parts 203. As shown in enlarged cross-sectional view of (d), a force acts on the cells in an upward direction (the direction of arrow 216) due to the viscosity of the solution during the sucking of the cell solution, whereas, gravity is in the 217 direction, which is a direction opposite to that of the suction direction. The sedimentation of the cells caused by gravity operates in a direction to separate the cells from the two-dimensional array chip. Thus, the suction force for the cells operates only at the cell capture parts 203, which prevents cell adsorption to regions other than the cell capture part on the two-dimensional array chip. While this embodiment utilizes gravity as the repulsive force in the direction which separates the cells from the two-dimensional array chip, use of other repulsive forces will be described later.

The nucleic acid capture part 210 may be composed of a porous material or beads (preferably, magnetic beads) and the like, and a nucleic acid probe for capturing the nucleic acids extracted from the cells may be immobilized. The nucleic acid probe includes a nucleic acid capture sequence which hybridizes with the nucleic acids extracted from the cells and a cell recognition sequence which is different corresponding to the respective cell capture parts. The single cell analysis is possible by using the product in which the nucleic acids captured by such nucleic acid probe are amplified. The nucleic acid probe can be appropriately designed by a person skilled in the art in accordance with the purpose of the analysis, the target to be analyzed (mRNA, genomic DNA, ncRNA, and the like), the configuration of the device to be used, the type of the amplification reaction, and the like.

Figure 1:
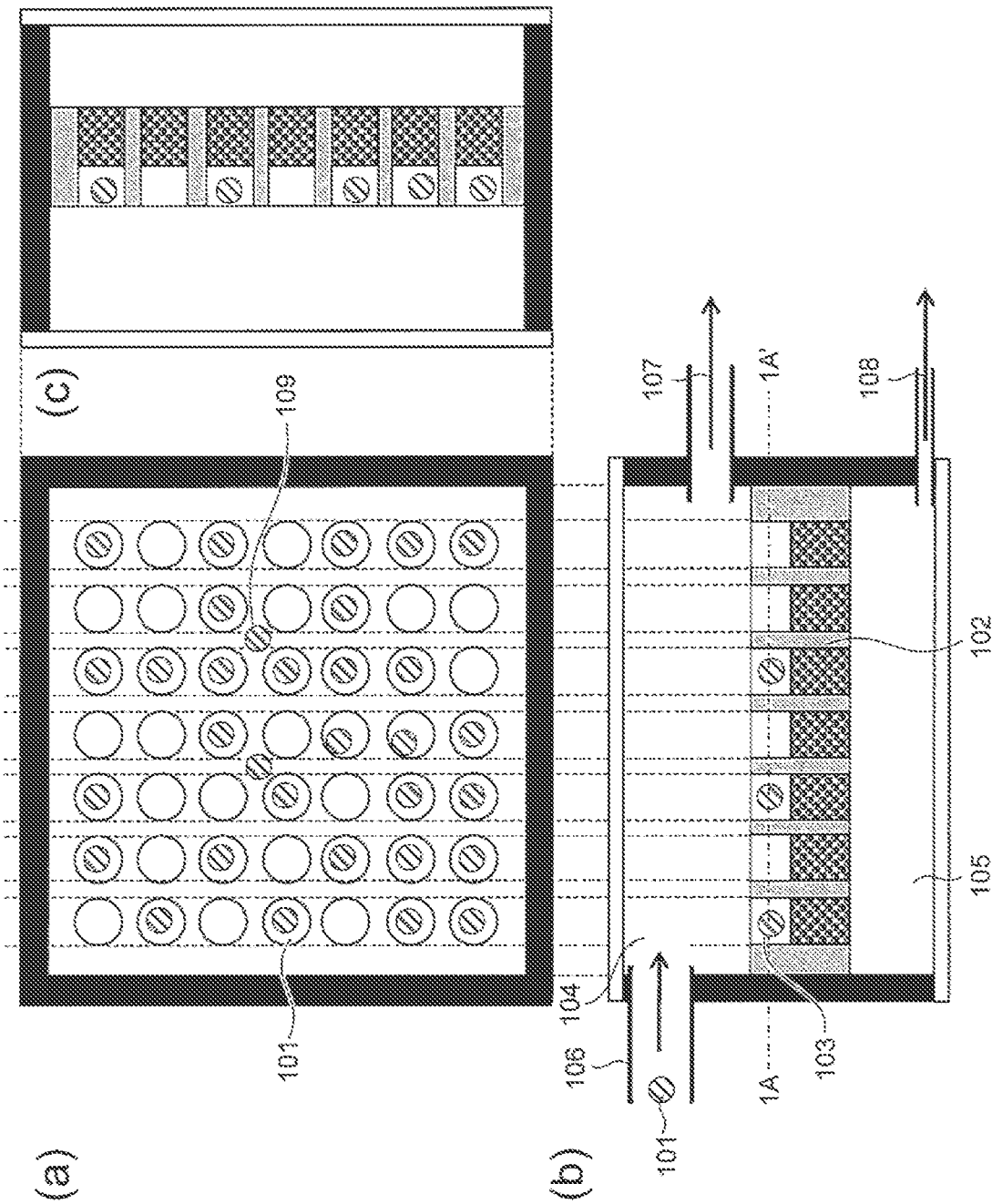
FIG. 1 is a figure showing a basic configuration of the device described in Patent Document 1 which is technology related to the present invention.

The cell solution is introduced from the cell introduction port 211. In this case, the region 214 is filled with the cell solution in a vertically inverted form with regard to the conventional example shown in FIG. 1, and the cell solution is sucked from the sample collection port 212. Subsequently, a single cell is adsorbed on the cell capture parts 203 by applying a negative pressure to suck the solution from the upper outlet 207, which feature is the same as the device of the conventional example. However, the device according to the present invention is different from the device of the conventional example in that the device is controlled to have the gravity work in a suitable direction.

The suction force that causes the cells to approach the two-dimensional array chip during cell suction needs to be stronger than gravity which is applied in the opposite direction. This strong suction is effective, particularly when the negative pressure which is applied to the upper outlet is close to 1 atm, and the pressure on the inside of the region 215 is set lower than the saturated vapor pressure of the cell solution. A continuous suction may be necessary to make the internal pressure lower than the saturated vapor pressure, thus, a continuous suction pump such as a diaphragm pump may be more effective than a pump using a syringe having a limited suction volume. Another method for realizing a strong suction force which overcomes gravity is a method which disposes a three-dimensional porous member. When disposed in the region 215, the three-dimensional porous member has the properties that the aqueous solution contacted is quickly absorbed due to the capillary phenomenon, and, the absorbed aqueous solution can be discharged to the outside, in particular, in a direction toward not being in contact with the nucleic acid capture part 210. By discharging the absorbed aqueous solution, the solution absorption performance due to the capillary phenomenon of the three-dimensional porous member can be maintained. By utilizing the capillary phenomenon of the three-dimensional porous member, the solution retained in the nucleic acid capture part 210 can be sucked more rapidly, compared to the case when merely applying a negative pressure in the conventional example shown in FIG. 1, and further, the ability that the cell capture parts 203 absorb cells can be improved. The embodiment using the three-dimensional porous member is explained in the description of the configuration for efficiently collecting the nucleic acid amplification product when steps up to nucleic acid amplification are performed on the device.

The force applied to the cells in the direction which separates the cells from the two-dimensional array chip is not limited to gravity. For example, it is possible to apply a repulsive force to the cells in the vicinity of the two-dimensional array chip to prevent the adsorption of cells on the two-dimensional array chip by subjecting the two-dimensional array chip (substrate) to a surface treatment having a negative charge relative to the two-dimensional array chip. Further, this can be realized even by coating the surface with a coating agent such as MPC polymer or polyethylene glycol.

Furthermore, it is also possible to apply a force in the direction which separates cells from the two-dimensional array chip by dielectrophoresis. This will be described in detail in Example 1-4.

Further, in another aspect, the three-dimensional porous member may be provided adjacent to the two-dimensional array chip, by which the cell analysis device of the present invention accelerates the suction of cells due to the capillary phenomenon and reduces the influence of sedimentation caused by gravity on the cells. The cell analysis device of the present invention, when provided with a three-dimensional porous member, similarly, provides a means for separating the two-dimensional array chip and the three-dimensional porous member during the amplification reaction so that the amplification product amplified on the two-dimensional array chip is not adsorbed on the three-dimensional porous member. Specifically, the cell analysis device of the present invention includes a solution introduction channel for introducing a solution containing cells; a two-dimensional array chip having a plurality of cell capture parts and nucleic acid capture parts, the cell capture parts being provided adjacent to the solution introduction channel and each being capable of capturing a single cell, and each of the nucleic acid capture parts being provided corresponding to each cell capture part of the plurality of cell capture parts and capturing a nucleic acid extracted from the cell having been captured by the cell capture part; a discharge channel having a three-dimensional porous body which absorbs a solution retained in the nucleic acid capture part and for discharging the solution; and a separation control part for controlling separation between the nucleic acid capture part and the discharge channel. The separation control part performs separation control such that, after the nucleic acid is captured by the nucleic acid capture part, a product amplified from the captured nucleic acid is not introduced into the discharge channel.

Figure 3:
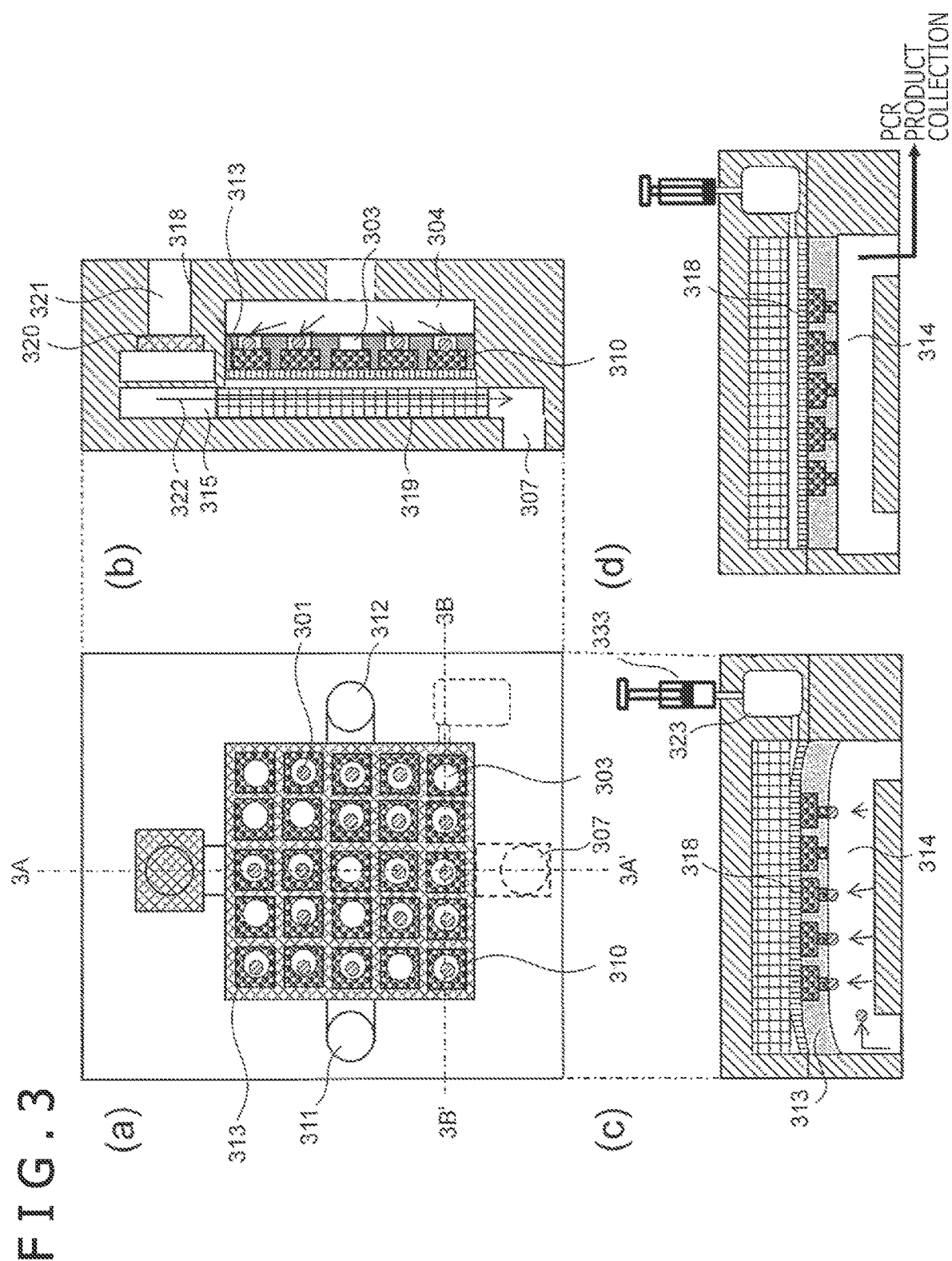
FIG. 3 is a figure showing an embodiment having the configuration of the cell analysis device according to another aspect of the present invention.

FIG. 3 is a figure showing an embodiment of the configuration of the cell analysis device of the aforementioned aspect of the present invention, where (a) shows a bottom view (a plan view seen from the bottom), (b) shows a cross-sectional view in the 3A-3A' cross section, and (c) and (d) show cross-sectional views in the 3B-3B' cross section.

The cell analysis device according to another aspect of the present invention relates to the configuration characterized in providing a means that can efficiently collect the amplification product from the nucleic acids extracted from cells to the outside. There is provided, in the same manner as the above aspect, a two-dimensional array chip (313) having a plurality of cell capture parts 303 and nucleic acid capture parts 310, each of the cell capture parts being capable of capturing a single cell, and each of the nucleic acid capture parts being provided corresponding to the respective cell capture parts and being capable of capturing a nucleic acid extracted from the cells having been captured on the cell capture parts. It is also the same as the above aspect that a lower region 314 which holds a cell solution introduced from a cell introduction port 311 is disposed adjacent to the two-dimensional array chip, and an upper region 315 of the opposite side is connected to an upper outlet 307. Furthermore, it is also the same that a pump or a syringe is connected to the upper outlet 307, a negative pressure can be applied to the nucleic acid capture part 310 and the cell capture parts 303 on the two-dimensional array chip by applying a negative pressure to the upper outlet 307, and the cell solution within the region 314 is sucked into the cell capture parts 303 are also similar. However, the present aspect is different in the point that a means for separating the three-dimensional porous member from the two-dimensional array chip is provided in a configuration for capturing cells by increasing the suction force by disposing the three-dimensional porous member in the upper region. A "storage tank" (the space for introducing air or a separation solvent such as a nonpolar solvent (for example, mineral oil)) 323 of FIG. 3, and a syringe 333 as a means for injecting air or a separation solvent in the region between the three-dimensional porous member and the two-dimensional array chip are provided as the separation means. In the present aspect, the two-dimensional array chip may be prepared with a resilient material (here, a PDMS resin), thus, by applying a negative pressure for suction to the upper outlet 307, the two-dimensional array chip is bent by the negative pressure application to be in close contact with the three-dimensional porous member 319 as in the two-dimensional array chip shown by 313 in FIG. 3(C). Suction by the capillary effect of the three-dimensional porous member becomes possible by such close contact. By stopping the application of negative pressure and injecting air or separation solvent between the three-dimensional porous member 319 and the two-dimensional array chip 313 from the "storage tank" 323 of the respective element, the migration of a substance through the solution is blocked. The adsorption of DNA, which is the amplification product, on the inner wall of the three-dimensional porous member can be prevented by this blocking.

Specifically, in order to maintain the state in which the numerous beads constituting the nucleic acid capture parts 310 in the two-dimensional array chip are packed, a membrane for preventing bead outflow (hydrophilic porous membrane) 318 is brought into close contact with the back surface of the two-dimensional array chip 313. The close contact of the three-dimensional porous member and the two-dimensional array chip may be accurately performed by the close contact of a bead holding membrane 318 and the three-dimensional porous member. Here, the membrane for preventing bead outflow 318 functions integrally with the two-dimensional array chip 313, thus, the suction by the capillary effect is effective.

As the separation means, an actuator can be connected to the three-dimensional porous member to change the distance between the three-dimensional porous member and the two-dimensional array chip so as to separate the three-dimensional porous member and the two-dimensional array chip.

Furthermore, it is also possible to separate the three-dimensional porous member and the two-dimensional array chip by providing an isolation membrane such that the amplification product does not reach the surface of the three-dimensional porous member while keeping them in close contact with each other. This step may be performed, for example, by disposing between the three-dimensional porous member and the two-dimensional array chip, an ultrafiltration membrane or a gel membrane having a pore size which prevents the passing through of molecules (for example, DNA molecule) having the molecular size of the amplification product.

The three-dimensional porous member used in the present invention can be a material having pores ranging in size from several tens of nanometers to zero point several micrometers in a random manner, and having a surface hydrophilicity to the extent that an aqueous solution can be absorbed by the capillary phenomenon produced by the presence of the pores. Specific examples may include a porous glass material, a glass fiber assembly (for example, a material in which glass fibers are arranged in the same direction and bundled), a glass bead assembly (the average particle diameter is preferably in the range of 0.1 to 30 µm) and the like. The three-dimensional porous member may preferably be not easily deformed to lower the possibility that the absorbed solution may unintentionally discharged and flows back to the nucleic acid capture part 310 and the cell capture part 303. The hydrophilic surface of the three-dimensional porous member can be characterized by either a water contact angle measured using pure water being 90° or less, preferably 80° or less, more preferably 50° or less, and most preferably 40° or less, or when dropping 1 μL of pure water on the three-dimensional porous member having a volume sufficient to maintain 1 μL of liquid, absorbing the dropped droplets within 10 seconds, preferably within 5 seconds, more preferably within 3 seconds, and most preferably within 1 second. Note that, the expression that the droplets are absorbed by the three-dimensional porous member means that the presence of the droplets cannot be confirmed visually when observed from a plane perpendicular to the surface of the three-dimensional porous member.

Further, it may be preferable that the three-dimensional porous member constituting the solution holding part 319 is sufficiently larger in pore diameter than that of the pores belonging to the nucleic acid capture part 310 which is composed of the porous membrane, beads, etc. For example, the average pore diameter may preferably be 0.2 μm or more, and especially 3 μm or more. If the pore diameter has such size, an excessively large pressure loss does not occur when a gas such as air passes through the solution holding part 319. Further, if the pore diameter of the three-dimensional porous member is large as stated above, a sufficient pressure difference can be produced between the upper and lower part of the nucleic acid capture part 310 when the negative pressure is applied from the upper outlet 307.

Preferably, the flow channel including the solution holding part 319 and communicating with the upper outlet 307 also communicates with an intake port 321 which opens to the outside of the apparatus through a pressure adjustment member 320. In the apparatus of FIG. 3, the intake port 321 opens to the outside in the upper direction of the apparatus. In the case where the intake port 321 is provided, when the negative pressure is applied from the upper outlet 307, the outside gas is taken in from the intake port 321 through the pressure adjustment member 320. This generates an airflow 322, which causes the solution absorbed in the solution holding part 319 to be discharged. With the configuration including the intake port 321, the solution holding part 319 can absorb the solution by the capillary phenomenon only when a negative pressure is applied from the upper outlet 307. That is, the solution holding part 319 can absorb the solution again by the capillary phenomenon only for the volume of the solution that has been discharged by the solution holding part 319. Further, in the configuration without the intake port 321, the solution may not reach the solution holding part 319 by only filling the upper region 314 with the solution, so that absorption does not start; while on the other hand, if absorption starts, the absorption does not stop until the solution holding part 319 is fully filled, which means that the controllability is insufficient. In this case, the controllability can be compensated by providing the intake port 321. It may be preferable to further provide an air valve in the intake port 321, as the controllability of the absorption of the solution is further improved.

The pressure adjustment member 320, when a gas passes therethrough, preferably produces a pressure loss larger than the pressure loss produced when a solution passes through the nucleic acid capture part 310. By providing such pressure adjustment member 320, when a negative pressure is applied from the upper outlet 307, the negative pressure is applied not only to the intake port 321, but also sufficiently to the solution holding part 319, the nucleic acid capture part 310 and the cell capture part 302. As for the pressure adjustment member 320, the balance may be good from the viewpoint of the viscosity difference between air and water if using a material having a pore smaller than the pore of the nucleic acid capture part 310, for example, a material having an average pore diameter of about ⅕ to about 1/10, more preferably about ⅐ to about ⅑, and especially, about ⅛ of the pore of the nucleic acid capture part 310, for example.

Note that, the present inventors already filed an international patent application for a cell analysis device provided with a three-dimensional porous member (PCT/JP2015/077849 filed Sep. 30, 2015). The contents described in the specification, claims and drawings of the application are herein incorporated by reference as is.

Figure 4:
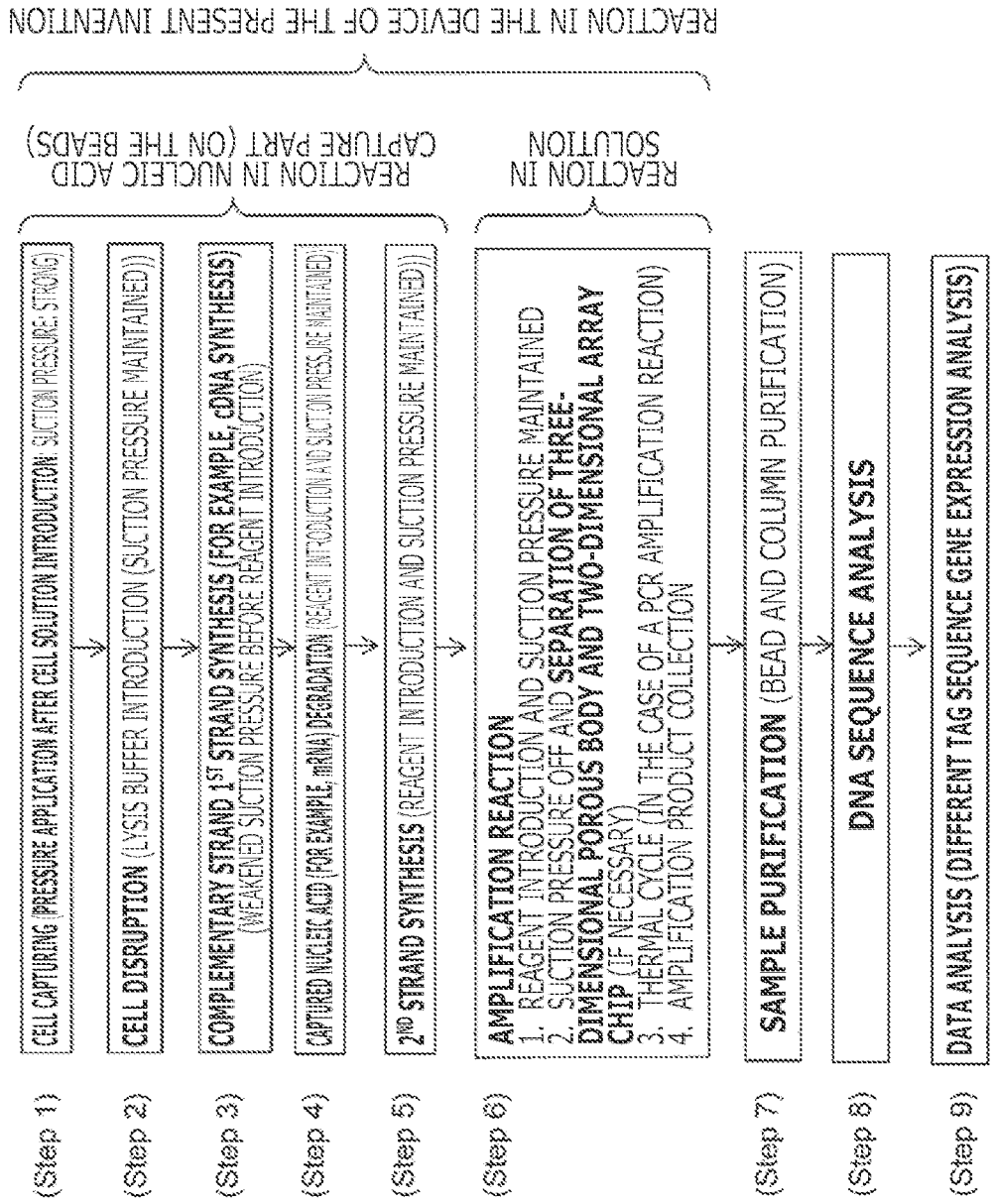
FIG. 4 is a flow diagram of a cell analysis method using the cell analysis device according to the present invention and a figure showing the separation timing.

FIG. 4 shows a flow diagram of the cell analysis method using the device according to the present invention. The timing at which the three-dimensional porous member is separated from the two-dimensional array chip is explained with reference to the diagram.

After the cells are captured on the cell capture part 303 in the first step as stated above, then in (Step 2), the cells are disrupted by a lysis buffer and the like in a state in which a negative pressure is applied from the upper outlet 307, and the nucleic acids extracted from the cells (for example, mRNA) are captured by the nucleic acid probe immobilized on the nucleic acid capture part 310. In (Step 3), using the nucleic acids captured on the surface of the nucleic acid capture part 310, a 1st strand of the complementary strand (for example, cDNA) of the captured nucleic acid (for example, mRNA) can be synthesized by introducing a reagent containing an enzyme to the nucleic acid capture part. In (Step 4), a 2nd strand can be synthesized by introducing a second DNA probe corresponding to a gene to be measured and an enzyme reagent to the nucleic acid capture part. Until this point, a reaction has occurred at the surface of all of the nucleic acid capture parts, and necessary reaction products may be immobilized on the surface. In the subsequent amplification reaction (for example, PCR), the amplification product is released from the surface, and collected from the device as a final product. At this time, in order to prevent the amplification product from being adsorbed on the inner wall of the three-dimensional porous member, the suction force is turned off after the reagent containing the enzyme and the substrate necessary for the amplification reaction are introduced to the nucleic acid capture part by suction, and air or a separation solvent for separation is injected between the three-dimensional porous member and the two-dimensional array chip from a "storage tank" 323 by pressing the syringe 333. Therefore, the amplification product is blocked from migrating from within the two-dimensional array chip to the three-dimensional porous member, and the adsorption can be prevented. During amplification, the amplification product spreads out from within the two-dimensional array chip by diffusing into the region 314.

The timing of the separation by the injection of air or the separation solvent may also be the timing before the amplification reaction (for example, PCR cycle reaction) after reagent introduction. However, it may be better to separate the three-dimensional porous member and the two-dimensional array chip after completing several cycles of the amplification reaction prior to the migration from the nucleic acid capture part to the three-dimensional porous member by diffusion. The influence of the migrating of the solution due to temperature variation can be suppressed to a minimum by performing the separation at such timing.

After the completion of the amplification step, the amplification product is collected from the sample collection port 312 by suction. At this time, the cell introduction port 311 is opened, and the solution migrates from 311 toward 312. DNA strands (especially, short DNA strands) of lengths which are not necessary for analysis are contained in the obtained amplification product, thus, in (Step 7), purification is conducted to remove these DNA strands, and the sequence analysis is performed by a next-generation sequencer in (Step 8). Finally, obtaining the results of the single cell analysis by rearranging the sequences obtained in the tag sequences corresponding to the cell capture positions (Step 9) may be similar to the conventional example. Note that, the amplification of the nucleic acid may preferably be PCR amplification, but not limited thereto, and it is possible to use other amplification methods such as rolling circle amplification (RCA) reaction, NASBA method, and the LAMP method. These other amplification methods are well-known in the technical field, thus, a person skilled in the art could appropriately select a nucleic acid probe and a reagent(s) to be used.

Further, when separating the three-dimensional porous member from the two-dimensional array chip with an actuator, the separation may also be performed at the same timing as stated above.

Furthermore, in the separation method using the ultrafiltration membrane or the gel membrane, the migration of the amplification product to the porous member may be blocked at all times, thus, it is not necessary to set the timing of the separation. Herein, the amount of migration of the nucleic acid of the amplification product can be reduced to $1/10$ or less in a state in which there is no negative pressure application by setting the pore size of the ultrafiltration membrane or the gel membrane to 1 to 10 nm, for example, 5 nm (30 kDa).

EXAMPLES

The present invention will be explained in greater detail below using examples; however, the present invention is not limited to these examples.

(Example 1-1) Manufacture of the Device

Figure 5:
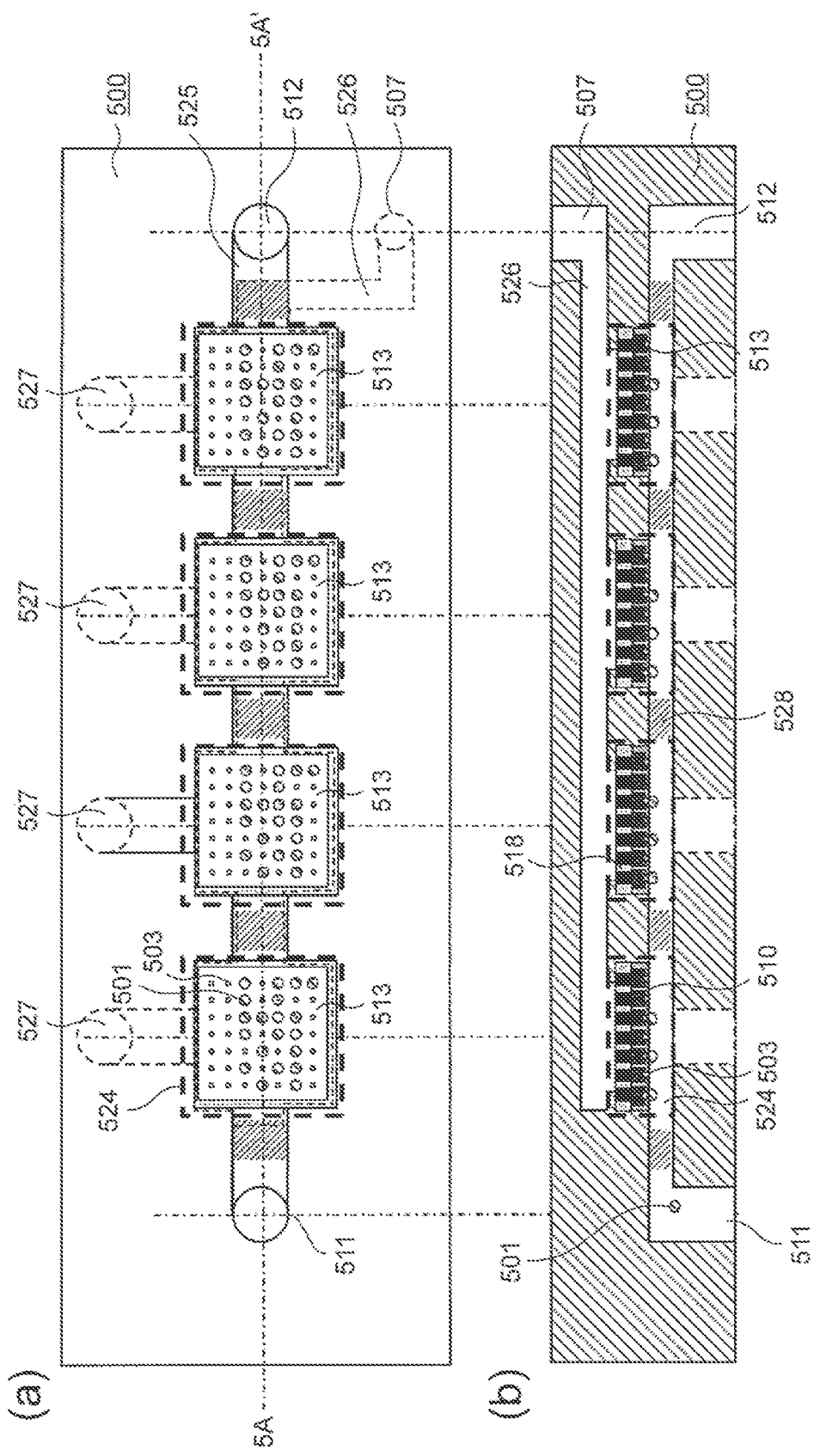
FIG. 5 is a figure showing an outline of the configuration of the device manufactured in Example 1-1.

FIG. 5 is a figure showing an outline of the configuration of the device manufactured in the present example, where (a) shows a bottom view (plan view seen from below), and (b) shows a cross-sectional view in the 5A-5A' cross section. The device 500 includes a plurality of reaction chambers 524 each of which includes a two-dimensional array chip 513 arranged thereon, the two-dimensional array chip 513 includes sets of the plurality of cell capture parts 503 and nucleic acid capture parts 510 corresponding to the respective cell capture parts 503. A cell solution is caused to flow through a common flow channel 525 from a cell introduction port 511 toward a sample collection port 512, and then supplied on the two-dimensional array chip 513. The chip is thus filled with the cell solution. Separate inlets 527 may be used when separately introducing a reagent to the chips, specifically, for example, when introducing a reagent containing a primer having a tag sequence in purpose of identifying the chip.

A resin chip (square shape in which one side is 1.125 mm) made of dimethylpolysiloxane (PDMS) obtained by injection molding was used in the manufacture of the two-dimensional array chip 513, and a through-hole having a diameter in the range of approximately 3 to 10 μm which is smaller than the cells was formed to make the cell capture part 503. Note that, the manufacture of the two-dimensional array chip may be performed using a resin chip obtained by the injection molding using another resin (polycarbonate, cyclic polyolefin, polypropylene, and the like), or may be performed using a nanoimprint technology or a semiconductor process. The material used in the manufacturing of the two-dimensional array chip may preferably be a hydrophobic material, by which the adsorption of the cells, the reagent, and the like on the array chip can be reduced. By subjecting the surface of the substrate of such two-dimensional array chip to a treatment to prevent the adsorption of cells, it is also possible to apply a repulsive force to the cells (refer to Example 1-3).

A cylindrical space having a diameter of several tens of μm (for example, 10 to 50 μm) is provided directly below the cell capture part 503, and then the cylindrical space is filled with magnetic beads on which a probe for a nucleic acid capture is immobilized to thus constitute the nucleic acid capture part 510. The filling with the magnetic beads may be performed separately using an inkjet printer head. While the chip is vertically inverted, the nucleic acid capture part 510 is separately filled with 2 nL of a solution of the beads on which different sequences are immobilized according to each regions. The magnetic beads having a diameter of 1 μm may be suspended at a number density of $5 \times 10^9$/mL in the bead solution used for filling. Streptavidin is immobilized on the magnetic beads, and a DNA probe modified with 5' biotin is immobilized through streptavidin. The beads are made to have a diameter of several μm or less (for example, 1 μm or less) to increase the number of magnetic beads to be filled, and thereby improving the nucleic acid capturing efficiency. A membrane for preventing bead outflow 518 (porous membrane made of resin having a pore size of 0.8 μm: Isopore membrane, manufactured by Millipore Corporation) having a smaller pore diameter than the bead diameter is brought into close contact with the two-dimensional array chip 513 such that the filled magnetic beads do not flow out.

In the present example, gravity is used as the repulsive force, and the cells are prevented from contacting with and adsorbing on the regions other than the cell capture part on the two-dimensional array chip due to the sedimentation of cells with gravity. In the present example, gravity operates in the direction which separates the cells from the two-dimensional array chip, thus, it is necessary to suck the cells in order to overcome gravity. However, the nucleic acid capture part 510 of the two-dimensional array chip 513 is filled with magnetic microbeads, thus, by only applying a pressure difference to the upper and lower parts of the two-dimensional array chip 513 using the syringe, the cell solution does not flow at a sufficient flow rate and a sufficient suction force cannot be obtained. Therefore, in the present example, as a more preferred embodiment, the suction method is performed not by using the syringe, but by connecting the diaphragm pump to the upper outlet, which keeps the pressure in the region of the upper flow channel 526 at or below the saturated vapor pressure of an aqueous solution so as to evaporate and rapidly discharge the solution which reached the back surface of the two-dimensional array chip. Evaporating the solution in this way promotes the capillary effect of the nucleic acid capture part to thereby realize high-speed suction can be performed and to capture the cells against gravity.

(Example 1-2) Single Cell Analysis Method Using the Device

FIG. 4 is a flow diagram showing an outline of the single cell analysis method using the device of the present invention manufactured in Example 1-1 shown in FIG. 5. In the present example, (Step 1) cell capturing, (Step 2) cell lysis (disruption), (Step 3) complementary strand (1st strand) synthesis (for example, cDNA synthesis), (Step 4) captured nucleic acid degradation (for example, mRNA degradation), (Step 5) 2nd strand synthesis, and (Step 6) the amplification reaction are performed in the device. In the reaction until (Step 5), the reaction product may be immobilized on the nucleic acid capture part 510, and the reaction is a solid phase reaction. In (Step 6), the amplification product released from the two-dimensional array chip diffuses into a reaction reagent in the reaction chamber 524. After completion of the amplification reaction, the reagent containing the amplification product may be collected from the sample collection port 512 by suction.

Further, after completion of the complementary strand (1st strand) synthesis (for example, cDNA synthesis) of (Step 4), the two-dimensional array chip may be removed from the device and the chip may be submerged in the tube containing the reagent so as to collect the beads in the solution (Step 5). After that, the subsequent reactions may be performed in the tube (outside of the device).

(Step 7) is a purification step which removes by-products during amplification, which are unnecessary for nucleic acid sequence analysis. Furthermore, (Step 8) is a sequence analysis step using a next-generation sequencer, and any sequence analysis platform may be used as long as it is a sequencer with a high parallelism. The final step (Step 9) is data analysis step, which is a step for summarizing the sequence analysis results for the cell identification tags and chip tags, and for constructing the genetic analysis data of each single cell.

First, the step for capturing the cells in the cell solution by using the cell capture parts 503 on the two-dimensional array chip 513 is performed. To perform the step, the two-dimensional array chip 513 is filled with the cell solution by introducing the cell solution from the cell introduction port 511 and sucking the cell solution from the sample collection port 512. Next, by applying a negative pressure to the lower outlet 507, the cell solution passes through the cell capture parts 503 and the nucleic acid capture part 510 on the two-dimensional array chip 513, and the cells are captured on the cell capture parts 503. 501 of FIG. 5(a) shows the cells which are captured on the cell capture part. At this time, high speed suction can be performed by continuous exhaustion with the diaphragm pump and the capillary effect of the nucleic acid capture part to thereby overcome the sedimentation with gravity. The suction time may be within 1 minute per 1 μL. At this time, the adsorption of cells on the two-dimensional array chip due to the sedimentation is 10% or less.

To disrupt the cells, the two-dimensional array chip 513 is filled with a lysis buffer by introducing the lysis buffer from the cell introduction port 511 and sucking the lysis buffer from the sample collection port 512. Then, a negative pressure is applied to the lower outlet 507 so as to obtain the necessary suction rate. The applied negative pressure is made to the same as the pressure during the cell suction. Note that, to complete the cell suction, it may be effective to introduce a PBS buffer of approximately 1 μL before introducing the lysis buffer.

Next, the process proceeded to the step of complementary strand (1st strand) synthesis (for example, reverse transcription, cDNA synthesis). To achieve a necessary introduction rate with a reagent mix for the complementary strand synthesis (reverse transcription), the strength of the negative pressure is reset. After setting, the reagent is introduced from the cell introduction port 511 to fill the two-dimensional array chip 513 with the reagent. Then, to proceed with the complementary strand synthesis reaction (reverse transcription reaction), the temperature of the device is increased and maintained only for the time necessary for the reaction. Furthermore, the temperature is increased to 85° C. in order to inactivate the reagent (for example, reverse transcriptase). A washing buffer is introduced from the cell introduction port 511 to wash out and discharge unnecessary washing solution, and the negative pressure is reset to introduce and discharge the washing buffer in the nucleic acid capture part. The degradation of the captured nucleic acids (mRNA degradation) and the 2nd strand synthesis being the next steps are almost the same as the step of the complementary strand (1st strand) synthesis (reverse transcription).

The final step is the amplification reaction. The amplification reaction reagent mix is introduced to the cell introduction port 511, and a negative pressure is set so as to introduce the reagent mix to the nucleic acid capture part 510 at the necessary solution rate. The temperature cycle is started to perform the amplification reaction (especially, PCR), and the pressure setting is changed such that the syringe is simultaneously operated when the application of the negative pressure is stopped in the first to several cycles. After that, the temperature cycle is repeated until the necessary concentration of amplification product is achieved. Then, a negative pressure is applied to the lower outlet 507 to suck and collect the amplification product, and the collected amplification product solution is discharged in the tube.

Figure 6:
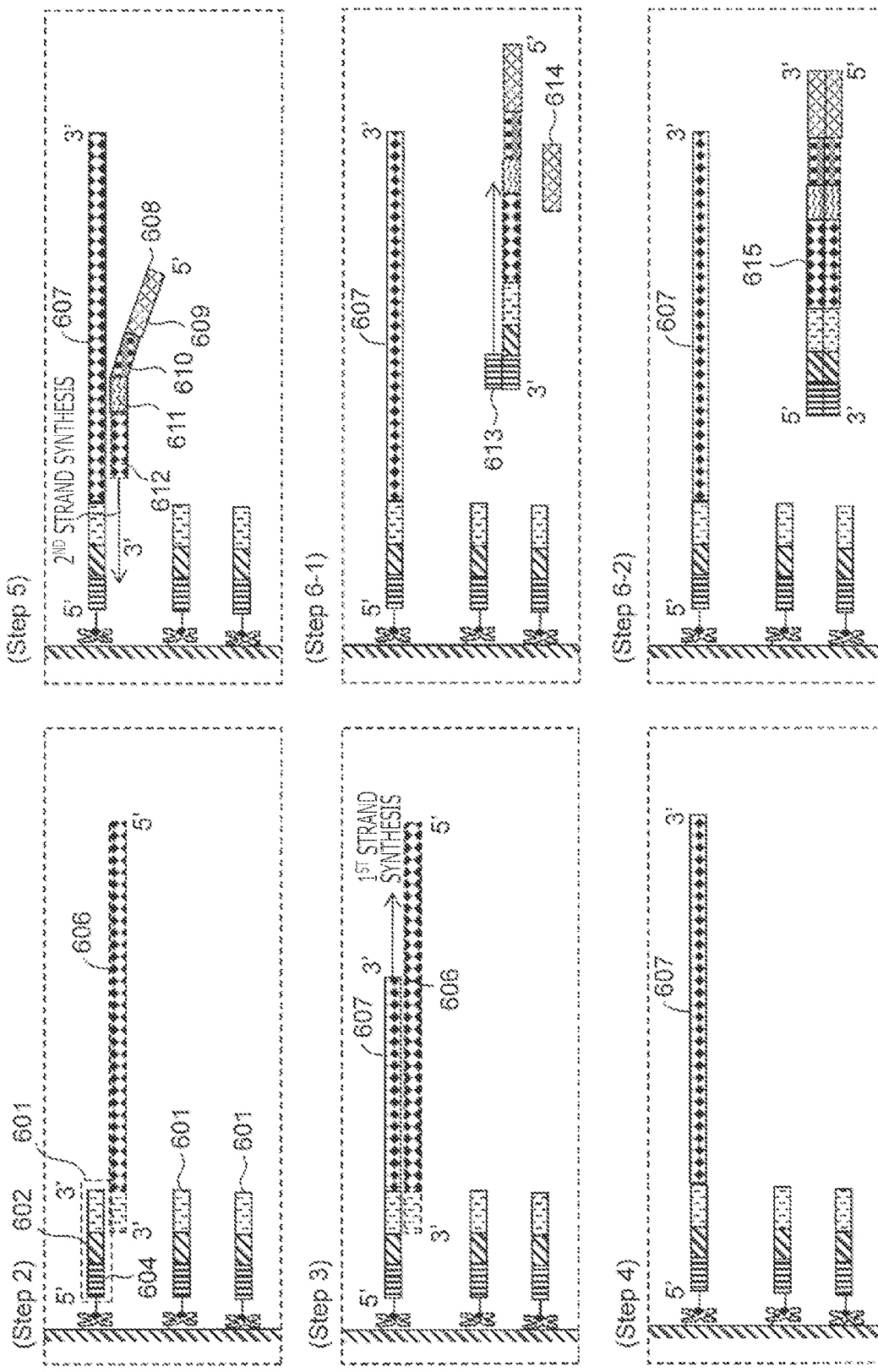
FIG. 6 is a figure showing a process of treating a nucleic acid in the analysis method using the cell analysis device according to the present invention.

Next, the preparation procedure of a sample for sequencing using the two-dimensional array chip 513 will be described in detail. FIG. 6 shows how the sample is prepared by treating the nucleic acid (for example, mRNA) captured by the nucleic acid capture part 510 of the device of the present example. This step can be divided into the disruption of the cells, after cell capturing (Step 1), the capturing of nucleic acid (mRNA) (Step 2), the synthesis of a complementary strand (1st strand) (for example, cDNA) (Step 3), the degradation of the captured nucleic acid (for example, mRNA) (Step 4), and nucleic acid amplification (PCR) and synthesis of 2nd strands into which known terminal sequences necessary for sequencing have been introduced (Step 5), and further, the steps of nucleic acid amplification (Step 6-1) and (Step 6-2).

After washing the cells with 500 μL of 1×PBS buffer without damaging the cells, 1000 cells suspended in 10 μL of 1×PBS buffer cooled to 4° C. are introduced from the cell introduction port 511, and sucked from the upper outlet 512 so that the reaction chamber 524 is filled with the solution. Therefore, the two-dimensional array chip 513 is filled with PBS buffer containing cells. Next, a negative pressure of 0.95 atm is applied to the lower outlet 507 by, for example, the diaphragm pump to suck the solution such that the solution flows through the cell capture part 503 toward the upper flow channel 526. The cells migrate along with the flow of the solution to reach the cell capture part 503. Since the diameter of the opening of the cell capture part 503 is smaller than the diameter of the cells, the cells are captured thereon. The captured cells serve as stoppers for the solution flow, thus, the solution flow moves to a cell capture part 503 that has yet to capture any cells. Therefore, the remaining cells migrate to capture parts that have yet to capture any cells and are captured.

When a desired number of cells have been captured, excess cells which have not been captured and the PBS buffer are discharged from the sample collection port 512. Next, after the lysis buffer (for example, a surfactant such as Tween 20) flowed from the cell introduction port 511 toward the sample collection port 512, and the two-dimensional array chip 513 is filled with the buffer, the solution is immediately sucked by applying a negative pressure to the lower outlet 507. All of the solutions hereinafter described pass through the nucleic acid capture part 510 of the two-dimensional array chip 513 by the same manner. At this time, as the membrane for preventing bead outflow 518 is a flow channel constituted from the porous material having a diameter of 0.8 μm, and has a large pressure loss. Thus, it may be easy for the lysis buffer to continuously and slowly flow for about 5 minutes through the cell capture part 503 toward the upper flow channel 526 by using such membrane for preventing bead outflow 518.

The captured cells 501 are disrupted by the lysis buffer, and the nucleic acid 606 (for example, mRNA) exits to the outside of the cell. However, the cell solution flowing in the vicinity of the cell capture part 503 continues to flow so as to be sucked into the pore constituting the cell capture part 503, thus, the nucleic acid 606 (for example, mRNA) reaches the nucleic acid capture part 510 through the cell capture part 503 without diffusing to the periphery. Therefore, the disruption of the cells and the capturing of the nucleic acid 606 (for example, mRNA) by a first DNA probe 601 immobilized on the bead of the nucleic acid capture part 510 are performed simultaneously by the introduction of the lysis buffer. The state is shown in Step 2 of FIG. 6.

Herein, in order to incorporate into the genetic analysis data the position information on the two-dimensional array chip 513 in which the cells are captured, i.e., the position coordinates of the cell capture part 503 arranged in a lattice-shape as shown in FIG. 5(a), a first DNA probe 601 in which a cell recognition sequence 602 having a sequence which is different in a corresponding manner with the respective cell capture parts 503 is immobilized on the bead surface of the nucleic acid capture part 510. In FIG. 6, the shaded parts at the left end of the diagram of each step show a wall surface to be immobilized, herein, the bead surface. The first DNA probe 601 has a sequence (for example, when capturing mRNA, a poly (T) sequence) complementary to the nucleic acid to be captured in the 3' terminal region, thus, the nucleic acid 606 (for example, mRNA) may be captured by hybridizing the probe with the sequence of the nucleic acid to be captured (for example, by hybridizing with the poly (A) sequence at the 3' terminal of mRNA). Further, a universal primer (604, Reverse) for the amplification reaction may be provided on the 5' terminal side.

In the present example, the first DNA probe 601 contains, from the 5' terminal, in the order of a universal primer (604, Reverse) for amplification having approximately 30 bases, a cell recognition sequence (602) having approximately 7 bases, and an oligo (dT) sequence having approximately 18 bases+a VN sequence having 2 bases. In the present example, a poly (T) sequence is used in a part of the DNA probe 601 for capturing in order to analyze the mRNA; however, a part of the sequence complementary to the sequence of the nucleic acid to be analyzed, or a random sequence can be used in place of the poly (T) sequence in order to perform microRNA and genome analysis. The sequence of such probe for capturing can be appropriately designed by a person skilled in the art based on conventional techniques.

Next, as shown in Step 3 of FIG. 6, the nucleic acid (mRNA) 606 captured by the first DNA probe 601 is used as a template to synthesize the 1st strand 607. In the present example, to synthesize the 1st cDNA from the mRNA, as a reagent for synthesizing the 1st strand, 58.5 μL of 10 mM Tris Buffer (pH=8.0) containing 0.1% Tween 20, 4 μL of 10 mM dNTP, 225 μL of 5×RT Buffer (SuperScript III, Invitrogen Corporation), 4 μL of 0.1M DTT, 4 μL of RNaseOUT (Invitrogen Corporation), and 4 μL of Superscript III (reverse transcriptase, Invitrogen Corporation) are mixed, and introduced from the cell introduction port 511 in the same manner as the previous step. While the aforementioned solution flowing very slowly from the reaction chamber 524 to the upper flow channel 526 in a state in which the gaps between the packed beads are filled with a solution containing a synthesis reagent (for example, reverse transcriptase) and a synthesis substrate, the temperature of the solution was slowly raised to 50° C. and the complementary strand synthesis reaction (1st strand synthesis reaction) was performed for about 50 minutes. As a result, the nucleic acid (for example, cDNA) immobilized on the surface of the plurality of beads for each cell is obtained as a library. Such libraries should be referred to as single cell nucleic acid (cDNA) library arrays, which are fundamentally different than the conventional normalized nucleic acid (cDNA) libraries obtained from many cells.

After the 1st strand 607 was synthesized, the entire device was maintained at 85° C. for 1.5 minutes to inactivate the synthesis reagent (for example, reverse transcriptase). After cooling to 4° C., 0.2 mL of 10 mM Tris Buffer (pH=8.0) containing RNase and 0.1% Tween 20, for example, was injected from the upper inlet 511 and sucked from the upper outlet 512 to fill the reaction chamber 524 with the solution. After that, the solution was discharged from the lower outlet 507 and the buffer in the reaction chamber 524 was removed from the upper outlet 512. By repeating this step for five times, the captured nucleic acid (mRNA) was degraded and the substances and the degraded substances remaining in the nucleic acid capture part were removed and washed out. Furthermore, washing was performed for five times in a similar manner with a liquid containing an alkaline denaturing agent and a washing liquid. A nucleic acid library array corresponding to all of the cells, for example, a cDNA library array can be constructed by the process up to this point for each of the captured cells as shown in Step 4 of FIG. 6.

Next, 69 μL of sterile water, 10 μL of 10× Ex Taq Buffer (TaKaRa Bio Corporation), 100 μL of 2.5 mM dNTP Mix, and 1 μL of ExTaq Hot start version (TaKaRa Bio Corporation) to which 10 μm of each of the universal sequences for amplification (Reverse) 609 is added were mixed, and this mixed reagent was introduced from the upper inlet 511 to the nucleic acid capture part 510 in the same manner as in the previous step. The method for separately introducing a second DNA probe 608 with a chip identification tag 610 will be described later. Then, after dissolving the secondary structure of the nucleic acid at 95° C. for 3 minutes, the gene-specific sequence 611 of the primer was annealed with the 1st strand as a template at 44° C. for 2 minutes. Step 5 of FIG. 6 shows the state in which the second DNA probe 608 is hybridized to the 1st strand, and the 2nd strand 612 is synthesized. The complementary strand elongation reaction is completed by increasing the temperature to 72° C. for 6 minutes.

The introduction of the second DNA probe 608 to the reaction chamber 524 is performed as follows. First, mineral oil is introduced from the cell introduction port 511, and discharged from the upper outlet 512. Next, the buffer solution containing the reagent flows through the upper flow channel 526 toward the separate inlets 527, and excess mineral oil within the reaction chamber is discharged from the separate inlets 527. In this manner, the regions filled with the buffer solution in the reaction chamber 524 at the lower portion of the two-dimensional array chip 513 are separated by the mineral oil. Such separation occurs because the inner wall of the reaction chamber 524 is hydrophilic, while on the other hand, a surface treatment is performed such that the region 528 between the reaction chambers is hydrophobic. Further, it is preferable that the 1st strand is firmly immobilized to the beads (for example, by biotin-avidin bonding) in order to maintain high reaction efficiency. After completion of the separation of the reaction chamber 524, a buffer solution containing the second DNA probe having the respective different chip identification sequences is introduced from the separate inlet 527, and the buffer solution is discharged from the upper outlet 512 through the upper flow channel 526. The vicinity of the nucleic acid capture part 510 is thereby filled with a different second DNA probe in each reaction chamber 524, and this probe hybridizes to the 1st strand. After completion of the synthesis of the 2nd strand, a large amount of the buffer solution flows from the cell introduction port 511 toward the sample collection port 512, and the mineral oil in the region 528 is washed away. As the flow channels only need to be connected, some mineral oil may remain in the region 528.

The final step is the amplification reaction by the universal primer as shown in Step 6-1 and Step 6-2 of FIG. 6. In the present example, a PCR reaction was performed, and 49 μL of sterile water, 10 μL of 10× High Fidelity PCR Buffer (Invitrogen Corporation), 10 μL of 2.5 mM dNTP mix, 4 μL of 50 mM MgSO$_4$, 10 μL of 10 μm universal primer for PCR amplification (Forward), 10 μL of 10 μm PCR the universal primer sequence for amplification (Reverse), and 1.5 μL of Platinum Taq Polymerase High Fidelity (Invitrogen Corporation) was mixed to prepare the reagent. Then, the reagent was introduced from the cell introduction port 511 in the same manner as the previous step. Subsequently, the entire device was maintained at 94° C. for 30 seconds, and a 3-step process of 94° C. for 30 seconds, 55° C. for 30 seconds, and 68° C. for 30 seconds was repeated 40 times. Then, at the end, the entire device was maintained at 68° C. for 3 minutes. After that, the entire device was cooled to 4° C. to perform the amplification step. This reaction is a universal reaction, and makes it possible to ensure uniform amplification efficiency among the chips by performing the amplification reaction under the universal conditions for all of the chips. For example, a PCR Purification Kit (QIAGEN Inc.) is used for purification in order to collect the amplification product solution accumulated in the solution and to remove the remaining reagents contained in the solution, such as free universal primer sequences for amplification (forward/reverse) and enzymes.

The obtained amplification product 615 is a sequence for which sequence analysis is possible, and is called a sequencing library. Even if an amplification bias occurs between the genes or molecules in this step, the amplification bias can be corrected with the use of the cell recognition tag after acquisition of the sequencing data, thus, highly accurate quantification data can be obtained. The gene expression levels per the cell identification sequences and the chip identification sequences can be obtained by performing sequence analysis of this sequencing library. Namely, the simultaneous analysis regarding a number of cells less than or equal to the number of the types of cell identification sequences simultaneously introduced into the device multiplied by the type of chip identification sequences is possible. The analysis of the number of cells which is significantly larger than the number of cell identification sequences introduced in advance in the two-dimensional array chip is thereby possible.

Note that, the present inventors already filed an international patent application for a cell analysis method enabling simultaneous performance of the genetic analysis of a single cell and the comprehensive genetic analysis of a cell population containing the cell (PCT/JP2014/073753 filed Sep. 9, 2014). The contents described in the specification, claims and drawings of the application are herein incorporated by reference as is.

(Example 1-3) Application Method of Repulsive Force Other than Gravity (Surface Treatment)

The two-dimensional array chip can be prepared using PDMS resin. The surface of the two-dimensional array chip (substrate) made of a PDMS resin is coated before injecting the beads constituting the nucleic acid capture part. Thus, a repulsive force acts on the cells in a direction which separates the cells from the two-dimensional array chip (substrate) in the vicinity of the two-dimensional array chip surface, and it is possible to prevent the adsorption of the cells on the chip surface. In the present example, by coating an MPC (2-methacryloyloxyethyl phosphorylcholine) polymer (Lipidure (Registered Trademark)-CM5206 manufactured by NOF Corporation), the adsorption rate of the cells can be reduced to 1/10 or less. As the coating method, a 0.5 w % ethanol solution was prepared, 2 μL per one chip was dropped on a PDMS resin membrane, the chip was covered with the solution, left standing for 5 minutes, and the chip was collected. The structure of the device is the same as FIG. 5, and the cells were hardly adsorbed and 95% or more of the cells were collected in all of the chips. Other than MPC polymer, a PEG (polyethylene glycol)-based coating agent (Blockmaster manufactured by JSR Life Sciences Corporation) and the like may be used as the coating agent, and any coating agent may be used.

(Example 1-4) Application Method of Repulsive Forces Other than Gravity (Configuration Using Dielectrophoresis)

Figure 7:
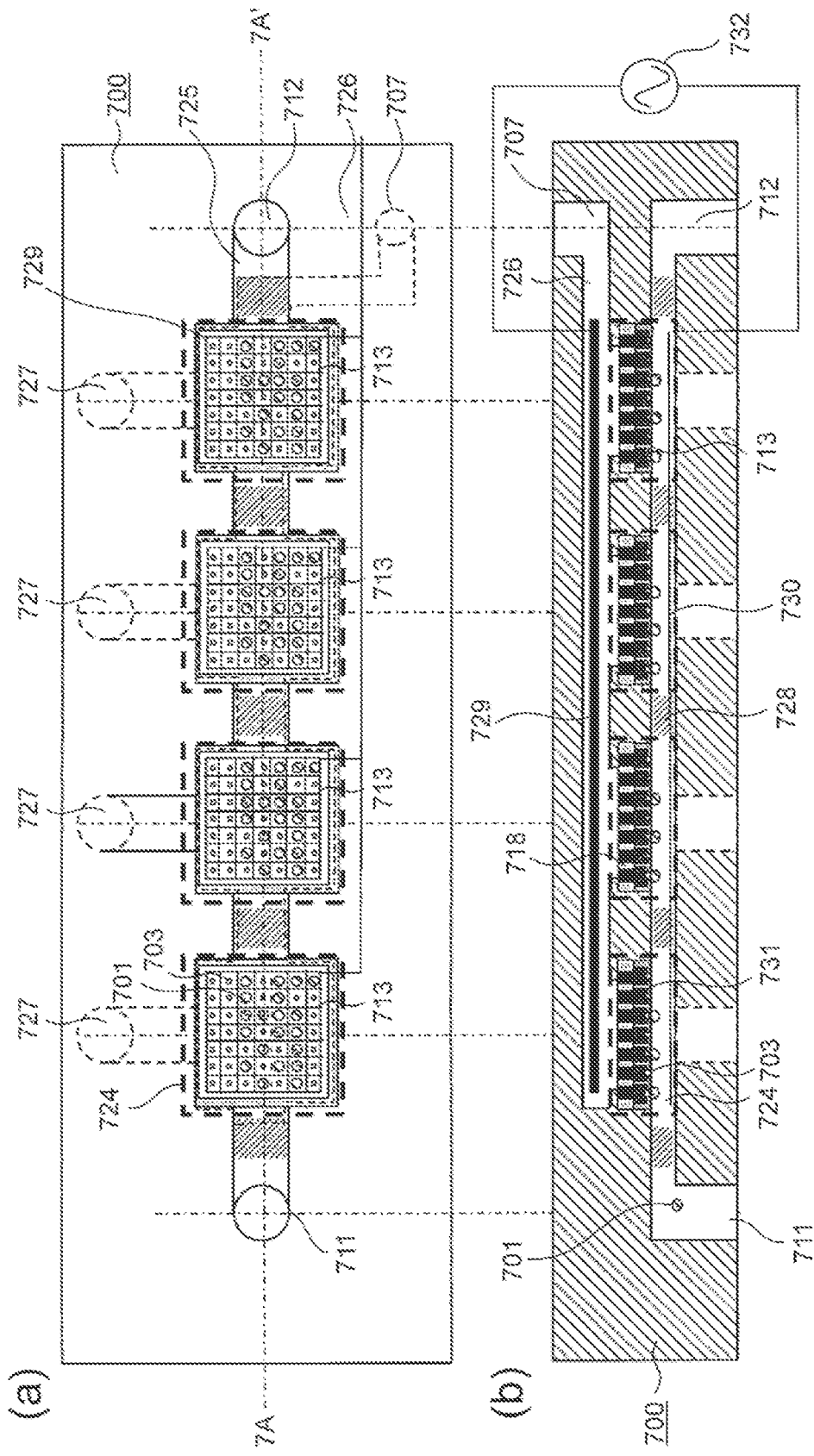
FIG. 7 is a figure showing an outline of the configuration of the device manufactured in Example 1-4.

FIG. 7 shows the configuration using dielectrophoresis to apply a repulsive force to the cells so as to reduce the adsorption of cells on the two-dimensional array chip. The differences from the basic configuration shown in FIG. 5 are that an electrode for dielectrophoresis is vertically disposed, that the beads of the nucleic acid capture part are configured by metallic gold microparticles instead of magnetic beads, and that a high frequency power supply is disposed.

The electrode configuration for preventing the adsorption of cells is as follows. An upper electrode 729 is disposed in an upper flow channel 726, and is a flat substrate made of platinum. A 1.1 mm square electrode disposed directly above the two-dimensional array chip and having approximately the same size as the two-dimensional array chip is connected in series in the same number as the number of chips. Further, the thickness of the electrode is set to 0.1 mm Because the applied voltage is low in the usage method of the present example, the possibility of corrosion is low, and the material may be a metal other than platinum. Further, in a lower electrode 730, a wire having a diameter of 0.1 mm is disposed in a lattice-shape and an electrode structure is molded by ultrasonic welding. Furthermore, as shown in FIG. 7(a), the wire is disposed so as to be positioned between the cell capture parts. Further, the nucleic acid capture part 731 is packed with gold microparticles having a diameter of 400 nm, and uses a thiol group on the surface to immobilize the DNA probe. By making the nucleic acid capture part from gold microparticles (gold colloid), a suction force acts toward the cell capture part by dielectric coupling. Note that, the AC voltage applied to both electrodes from a high frequency power supply 732 is a sine wave of 10 Vpp at several kHz and has a frequency lower than the frequency which reverses from a dielectric attractive force to a dielectric repulsive force. As a matter of course, the frequency may be higher than several MHz (the frequency is different depending on size of the cells and the dielectric constant) to make the dielectric force as a repulsive force and use antagonistically with the suction force.

Example 2

Figures 1, 8:
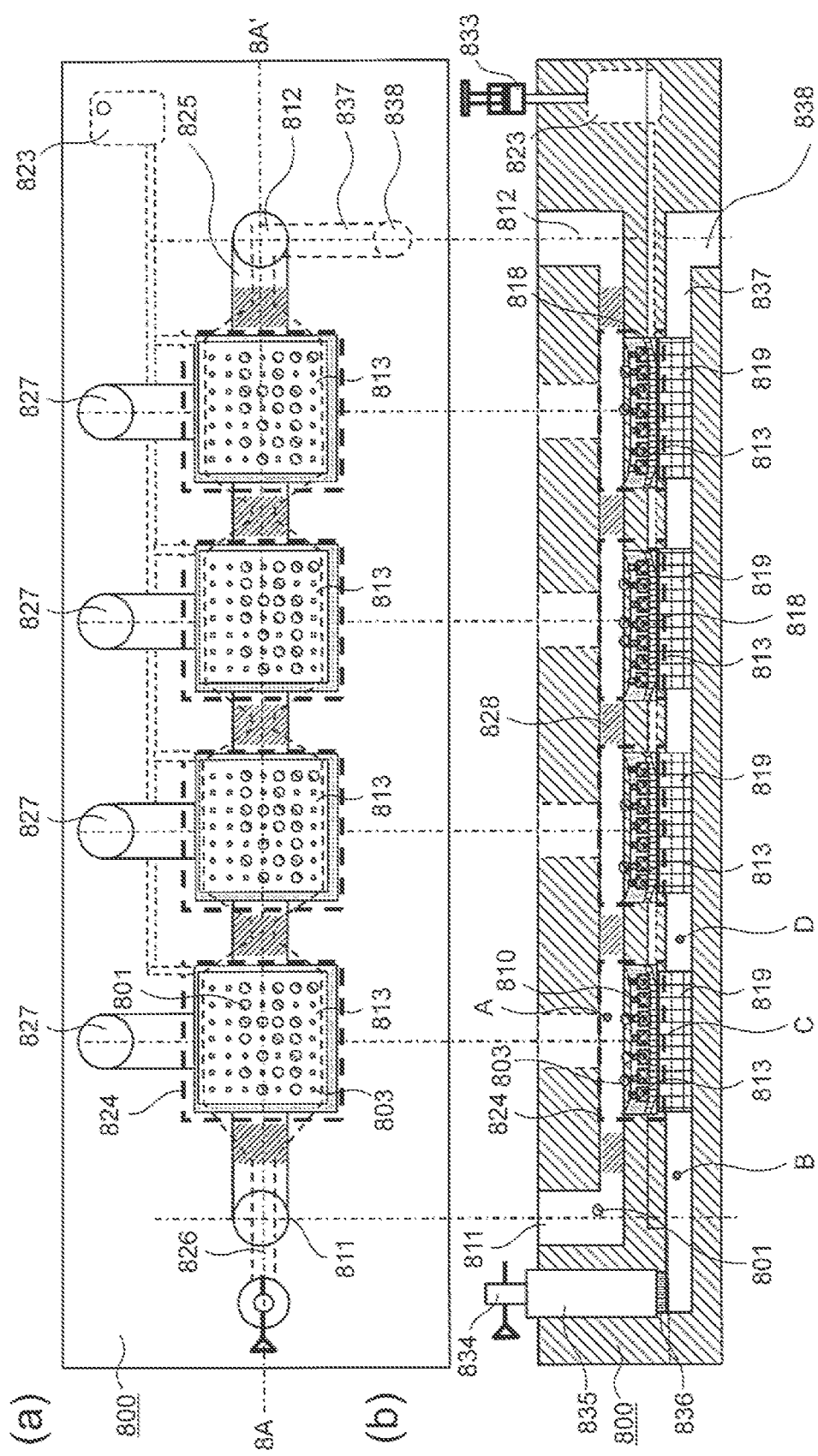
Figures 2, 8:
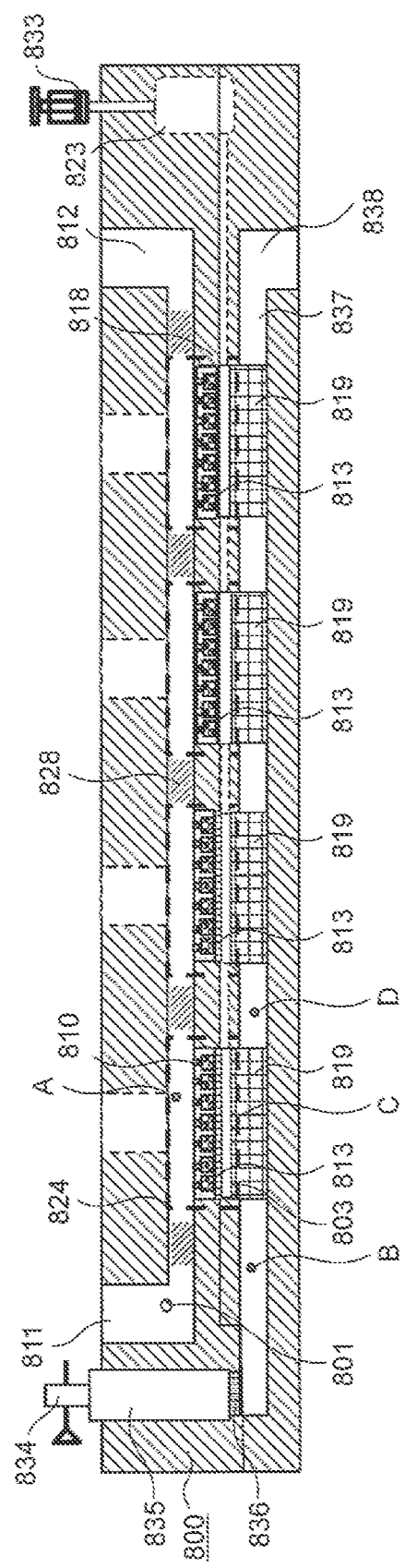

FIG. 8 is a figure showing an outline of the configuration of the device according to another aspect of the present invention; (a) shows a top view, and (b) shows the configuration at the time of cell solution suction in a cross-sectional view at the 8A-8A' cross section. Further, FIG. 8(c) shows a cross-sectional view when the three-dimensional porous member and the two-dimensional array chip are separated during the amplification reaction. The device of the present example is a configuration which does not arrange gravity and the suction force in the opposite direction as in Example 1 (may be placed in the opposite direction), increases the suction force by using the three-dimensional porous member, and reduces the influence of sedimentation with gravity to a minimum. At this time, the device structure and the operation method provided with a means for separating the three-dimensional porous member from the two-dimensional array chip in order to prevent the adsorption of the amplification product to the inside of the three-dimensional porous member disposed in a solution holding part 819 which is the problem to be solved will be described focusing on the points of difference from Example 1.

FIG. 8(b) is a cross-sectional view of the device while performing cell capturing. The two-dimensional array chip 813 is made of a PDMS resin having elasticity, and uses a porous membrane made of resin having a pore size of 0.8 μm (Isopore membrane, manufactured by Millipore Corporation) as a membrane for preventing bead outflow 818 for preventing the outflow of the beads which form a nucleic acid capture part 810.

The device 800 includes a plurality of reaction chambers 824, each of which includes a two-dimensional array chip 813 provided thereon, the two-dimensional array chip 813 having a plurality of cell capture parts 803 and nucleic acid capture parts 810 corresponding to the respective cell capture parts 803. A cell solution is caused to flow through a common flow channel 825 from a cell introduction port 811 toward a sample collection port 812, and then supplied on the two-dimensional array chip 813. The chip is thus filled with the cell solution. Separate inlets 827 are used when separate reagents are to be introduced into the chips, specifically, for example, when introducing a reagent containing a primer having a tag sequence for identifying a chip and the like.

A porous shirasu sintered member (Shirasu porous glass: SPG membrane, manufactured by SPG Technology Co., Ltd) which is a three-dimensional porous member is disposed in a lower flow channel 837 of the nucleic acid capture part 810, and is made as the solution holding part 819. By using this three-dimensional porous member, sucking at a high speed is possible, and the influence of sedimentation with gravity can be eliminated. The lower flow channel 837 is in communication with a lower outlet 838 and an intake port 835 which takes in the air, and is provided with a pressure adjusting filter 836 (in the present example, the porous membrane made of resin (Isopore membrane, manufactured by Millipore Corporation) having a pore diameter of 0.1 μm is used in consideration of the difference in viscosity between water and air) and an air valve 834 in the vicinity of the intake port 835. When capturing the cell in the cell capture part 803, the two-dimensional array chip 813 is filled with the cell solution, and then a negative pressure is applied by the syringe pump connected to the lower outlet 838 with the air valve 834 being open. Another pump such as a diaphragm pump can be used in place of the syringe pump.

The two-dimensional array chip is bent by applying a negative pressure to the lower outlet 838, and the membrane for preventing bead outflow 818 and the three-dimensional porous member (819) are in close contact with each other. Thus, the capillary effect of the three-dimensional porous member can be used to suck the cell solution at a high speed.

A high speed suction method using the capillary effect will be described below. In the device shown in FIG. 8, if the pressure relationships in position A (the upper part of the two-dimensional array chip 813), position B (the lower flow channel 837 between the solution holding part 819 and the pressure adjusting filter 836), position C (between the two-dimensional array chip 813 and the solution holding part 819), and position D (the lower flow channel 837 closer to the lower outlet 838 than the solution holding part 819) shown in the figure are set so as to satisfy the magnitude relationship of A>>B>C>D, the nucleic acid capture part 810 can be filled with the solution, and furthermore, the solution can come into contact with the solution holding part 819, and the capillary phenomenon is produced in the three-dimensional porous member constituting the solution holding part 819 to generate a large suction force. In the case where the pore size of the three-dimensional porous member is 10 μm, for example, it can be calculated that the suction force due to this capillary phenomenon produces a suction force of about 100 kPa in the cell capture part 803 (assumed to be a circular shape having a diameter of 5 μm) in the configuration of the present example. Thus, the cells can be sucked with substantially no influence on the sedimentation with gravity.

The air taken in from the intake port 835 passes through the solution holding part 819 due to the pressure difference between position B, position C and position D, and an aqueous solution absorbed by the solution holding part 819 is thereby discharged toward position D. The suction force due to the capillary phenomenon of the solution holding part 819 is recovered by this discharge, thus, as long as the suction from the lower outlet 838 continues, the suction force of the solution holding part 819 is maintained. On the one hand, if the suction from the lower outlet 838 is stopped, the inner wall of the pore of the three-dimensional porous member constituting the solution holding part 819 is rapidly filled with the aqueous solution, and the suction force may be lost.

Next, the separation method of the three-dimensional porous member from the two-dimensional array chip will be described. After filling the reaction chamber 824 with the reagent for the amplification reaction (PCR reaction) in the same manner as Example 1, the amplification reagent (PCR reagent) is introduced to the nucleic acid capture part by applying a negative pressure to the lower outlet 838. Then, the syringe 833 is pressed, and the mineral oil accumulated in the "storage tank" 823 is slowly injected between the membrane for preventing bead outflow 818 and the three-dimensional porous member over approximately 10 seconds. At this time, as the three-dimensional porous member is highly hydrophilic, most of the mineral oil which is a nonpolar solvent does not penetrate into the porous member. In this way, as shown in FIG. 8(c), the amplification reagent (PCR reagent) solution which remained in the three-dimensional porous member can be isolated from the amplification reagent (PCR reagent) in the nucleic acid capture part in the two-dimensional array chip. When air is used in place of the mineral oil, the air enters into the three-dimensional porous member, and the amplification reagent (PCR reagent) solution can be isolated from the two-dimensional array chip in the same manner.

(Example 2-2) Separation Due to the Moving Mechanism of the Three-Dimensional Porous Member In Example 2-1, a nonpolar solvent or oil for separation is injected; however, in the present example, it is also possible to separate the solution by increasing the interval between the three-dimensional porous member and the two-dimensional array chip at an appropriate timing. Specifically, a moving mechanism may be inserted directly below the three-dimensional porous member. The present example shows an example using an air pressure; however, a moving mechanism such as a servo mechanism may also be used.

The configuration for separating the two-dimensional array chip from the three-dimensional porous member by the air pressure is shown in FIG. 9. 939 is a polyethylene resin air bag. The air bag has a size of approximately 1×1 mm similar to the two-dimensional array chip and is designed such that the thickness of the air bag changes to about 0.1 to 0.3 mm by injecting air into the air bag with using a pump such as a syringe 940. When the syringe 940 is pressed to inject air, the two-dimensional array chip and the three-dimensional porous member are in close contact with each other and the suction of the solution due to the capillary effect becomes possible. The three-dimensional porous member is separated from the two-dimensional array chip by utilizing the fact that the internal pressure of air bag 939 decreases and the thickness thereof becomes thinner by drawing the syringe 940.

It may be possible to prevent the adsorption of the amplification product to the inner wall of the three-dimensional porous member by increasing the internal pressure of air bag before the amplification reagent (PCR reagent) introduction and by decreasing the internal pressure of the air bag after the start of the amplification reaction (for example, a PCR cycle).

Further, it may also be possible to prevent the adsorption of the amplification product to the three-dimensional porous member without performing the separation with a moving part. An ultrafiltration membrane having a pore size of approximately 5 nm can be used as the membrane for preventing bead outflow 918 in place of ISOPORE having a 0.8 μm pore size. In this case, the two-dimensional array chip and the three-dimensional porous member remain in close contact with each other during all of the steps; however, the application of negative pressure is turned off at the time of the amplification reaction. Thus, the speed at which the amplification product passes through the ultrafiltration membrane is greatly reduced. It is thereby possible to prevent the adsorption of the amplification product to the three-dimensional porous member.

Example 3

The present example describes the apparatus structure which combines a fluorescence microscope for observation of the captured cell with the device structure of Example 1.

Figure 10:
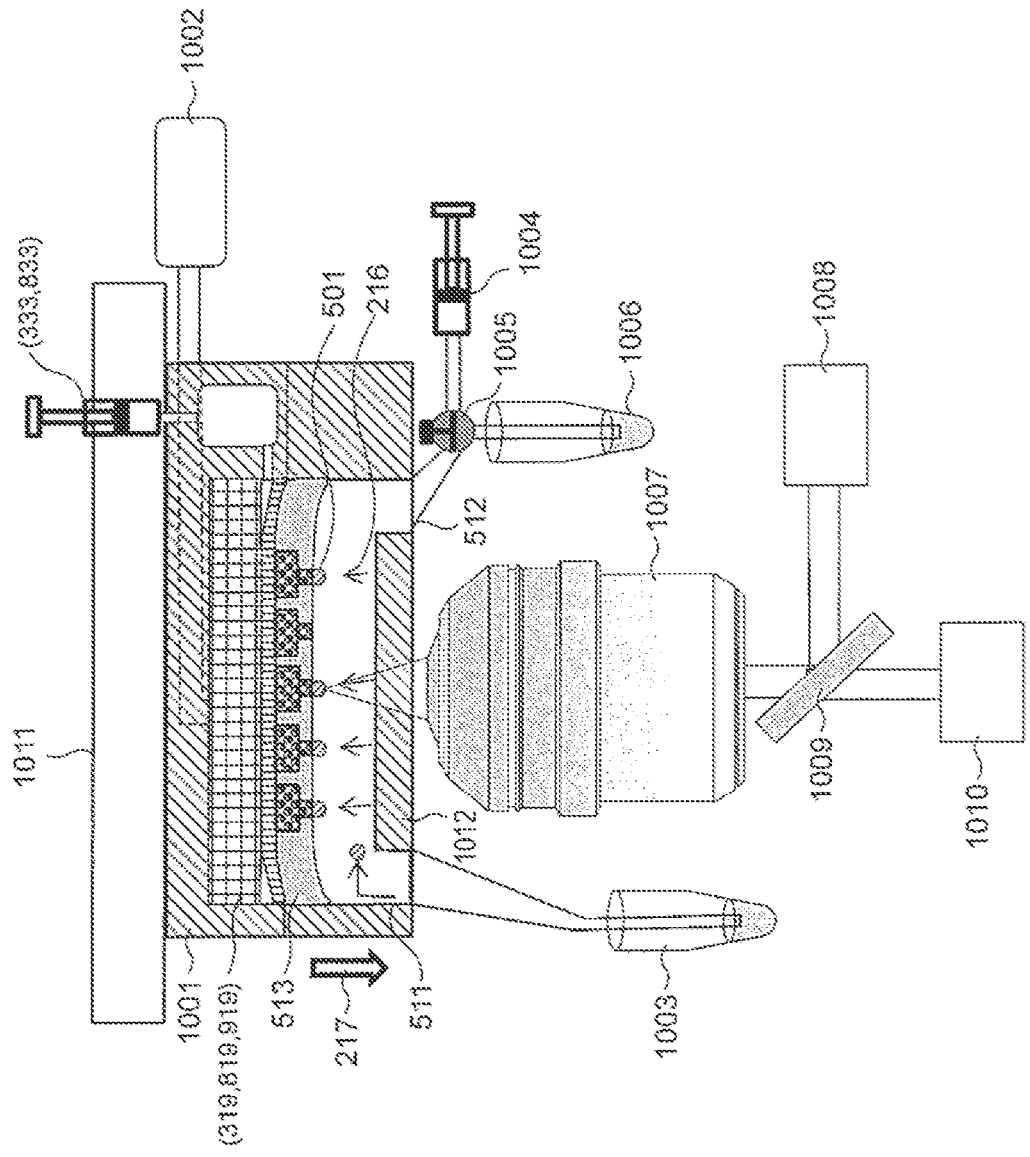
FIG. 10 is a figure showing an outline of the configuration of the apparatus according to Example 3.

A structural view is shown in FIG. 10. The configuration of a device 1001 is based on the basic configuration of Example 1. Note that the configuration of the device 1001 includes the three-dimensional porous members 319, 819, and 919 for high speed suction. Namely, the gravity direction 217 is set in the direction opposite to the cell suction direction 216. The two-dimensional array chip 513 in the figure shows the state during the sucking of the cell solution, and is in close contact with the three-dimensional porous members 319, 819, and 919. 501 is a captured cell.

Further, a diaphragm pump 1002 is used for the application of the negative pressure. The cells suspended in the buffer in a tube 1003 for the cell solution are introduced into the reaction chamber through the cell introduction port 511 by sucking with a syringe 1004. The excess cell solution and reagent are discharged in a tube 1006 for waste liquid through the sample discharge port 512 and a three-way stopcock 1005. The diaphragm pump 1002 is operated in a state in which the cell solution is introduced into the reaction chamber to capture the cells. To observe the state of at this time with the fluorescence microscope, an objective lens 1007, a laser light source 1008 having an excitation wavelength suitable for a fluorophore which stained the cells, a dichroic mirror 1009 for separating the excitation light and fluorescence from the cells, and a CCD camera 1010 as an imaging camera are provided as shown in FIG. 10. 1011 is an XYZ stage for focus adjustment and changing the image region. When observing cells with a fluorescence microscope, it is necessary to subject the cells to fluorescent staining Here, a staining method for staining the cell membrane is used. To acquire the fluorescence image via the microscope observation window 1012 on the device 1001, the material of the device including the window uses Acrylic (PMMA). As a matter of course, it is also possible to use other transparent resin materials (polycarbonate, cycloolefin and the like).

All publications, patents, and patent applications cited herein are herein incorporated by reference in their entirety.

DESCRIPTION OF REFERENCE CHARACTERS 101, 201, 301: Cell
102: Porous membrane
103, 203, 303: Cell capture part
104, 204, 304: Upper region
105: Lower region
106: Inlet
107, 207, 307: Upper outlet
108: Lower outlet
109: Cell
210, 310: Nucleic acid capture part
211, 311: Cell introduction port
212, 312: Sample collection port
213, 313: Two-dimensional array chip
214, 314: Lower region for holding cell solution prior to suction
215, 315: Upper region
216: Cell suction (force) direction
217: Gravity direction
318: Membrane for preventing bead outflow (hydrophilic porous membrane)

319: Solution holding part (three-dimensional porous member)
320: Pressure adjustment member
321: Intake port
322: Airflow
323: Storage tank
333: Syringe
500, 700, 800, 900: Device
501, 701, 801, 901: Cell
503, 703, 803, 903: Cell capture part
507, 707: Lower outlet
510, 810, 910: Nucleic acid capture part
511, 711, 811, 911: Cell introduction port (upper inlet)
512, 712, 812, 912: Sample collection port (upper outlet)
513, 713, 813, 913: Two-dimensional array chip
518, 718, 818: Membrane for preventing bead outflow
524, 724, 824, 924: Reaction chamber
525, 725, 825, 925: Common flow channel
526, 726, 826, 926: Upper flow channel
527, 727, 827, 927: Separate inlet
528, 728, 828, 928: Region between reaction chambers
601: First DNA probe
602: Cell recognition sequences
604: Universal primer
606: Nucleic acid (mRNA)
607: 1st strand
608: Second DNA probe
609: Universal sequence for amplification (Reverse)
610: Chip identification tag
611: Gene-specific sequence
612: 2nd strand
613: Universal primer
614: Universal sequence for amplification (Forward)
615: Amplification product
729: Upper electrode
730: Lower electrode
731: Gold microparticle nucleic acid capture part
732: High frequency power supply
819, 919: Solution holding part (three-dimensional porous member)
823: Storage tank
833: Syringe
834, 934: Air valve
835, 935: Intake port
836, 936: Pressure adjusting filter
837, 937: Lower flow channel
838, 938: Lower outlet
939: Air bag
940: Syringe
1001: Device (housing)
1002: Diaphragm pump
1003: Tube for cell solution
1004: Syringe
1005: Three-way stopcock
1006: Tube for waste liquid
1007: Objective lens
1008: Laser light source
1009: Dichroic mirror
1010: CCD camera
1011: XYZ stage
1012: Microscope observation window

The invention claimed is:

1. A cell analysis method in a cell analysis device which includes:
a solution introduction channel; and
a substrate having a plurality cell capture parts and a plurality of nucleic acid capture parts, the cell capture parts being in contact with the solution introduction channel and having a concavity capable of capturing a single cell, and each of the nucleic acid capture parts being provided in communication with a corresponding cell capture part and configured to capture a nucleic acid extracted from the single cell having been captured by the corresponding cell capture part; and
a discharge channel that is provided adjacent to the nucleic acid capture parts of the substrate and having a three-dimensional porous member,
the cell analysis method comprising the steps of:
introducing a solution containing cells to the solution introduction channel;
applying a negative pressure to the discharge channel to suck the solution from the solution introduction channel and adsorb the cells on the cell capture parts of the substrate and capturing the single cell on the corresponding cell capture part, the negative pressure bringing the substrate into contact with the three-dimensional porous member of the discharge channel;
applying a repulsive force in a direction which separates the cells from the substrate, and
applying a first pressure that is greater than the repulsive force, when the single cell is captured by the corresponding cell capture part, and having a force in the direction from the cell capture part to a corresponding nucleic acid capture part.

2. The cell analysis method according to claim 1, further comprising the steps of:
disrupting the single cell captured on the corresponding cell capture part in a state in which the negative pressure is applied to the cell capture part; and
capturing a nucleic acid extracted from the single cell by the corresponding nucleic acid capture part.

3. The analysis method according to claim 2, further comprising the step of:
supplying to the corresponding nucleic acid capture part, a nucleic acid probe having a sequence which hybridizes with the nucleic acid captured by the corresponding nucleic acid capture part, and an enzyme and a substrate for complementary strand synthesis which uses the captured nucleic acid as a template to perform complementary strand synthesis.

4. The analysis method according to claim 1, wherein when performing a nucleic acid reaction in the nucleic acid capture part, the force in the direction from the corresponding cell capture part to the corresponding nucleic acid capture part is larger than gravity and smaller than the first pressure.

5. The analysis method according to claim 1, wherein the repulsive force is a repulsive force caused by the substrate being placed in such a manner that the corresponding cell capture part captures the single cell in a direction counter to gravity.

6. The analysis method according to claim 1, wherein the repulsive force is a repulsive force caused by a surface of the substrate having been subjected to a treatment which prevents the adsorption of cells.

7. The analysis method according to claim 1, wherein the cell analysis device includes an electrode pair provided so as to sandwich the substrate, wherein the nucleic acid capture parts comprise metal microparticles, and the repulsive force is a repulsive force caused by a voltage applied to the electrode pair and dielectric coupling by the metal microparticles.

* * * * *